(12) United States Patent
Nonaka et al.

(10) Patent No.: US 6,171,519 B1
(45) Date of Patent: Jan. 9, 2001

(54) FERROELECTRIC LIQUID CRYSTAL MIXTURE

(75) Inventors: Toshiaki Nonaka, Iruma; Ayako Takeichi, Tokorozawa; Li Ji, Higashikurume; Kazuya Nagao, Kawagoe, all of (JP); Rainer Wingen, Hattersheim (DE); Javier Manero, Liederbach (DE); Barbara Hornung, Hasselroth (DE); Wolfgang Schmidt, Köln (DE)

(73) Assignee: Hoechst Research & Technology Deutschland GmbH & Co. KG, Frankfurt (DE)

( * ) Notice: Under 35 U.S.C. 154(b), the term of this patent shall be extended for 0 days.

(21) Appl. No.: 08/983,225

(22) PCT Filed: Jul. 17, 1996

(86) PCT No.: PCT/EP96/03154

§ 371 Date: Jun. 29, 1998

§ 102(e) Date: Jun. 29, 1998

(87) PCT Pub. No.: WO97/04039

PCT Pub. Date: Feb. 6, 1997

(30) Foreign Application Priority Data

Jul. 17, 1995 (JP) ...... 7-180339
Dec. 28, 1995 (JP) ...... 7-343288

(51) Int. Cl.[7] .......... C09K 19/34; C09K 19/32; C09K 19/12; G02F 1/133
(52) U.S. Cl. .......... 252/299.61; 252/299.62; 252/299.63; 252/299.65; 252/299.66; 252/299.67; 349/182
(58) Field of Search .......... 252/299.61, 299.62, 252/299.66, 299.65, 299.67, 299.63; 349/182

(56) References Cited

U.S. PATENT DOCUMENTS

| | | | |
|---|---|---|---|
| 4,976,887 | * 12/1990 | Takatoh et al. | 252/299.62 |
| 5,209,866 | 5/1993 | Reiffenrath et al. | |
| 5,323,624 | 8/1993 | Reiffenrath et al. | |
| 5,389,291 | 2/1995 | Reiffenrath et al. | |
| 5,443,752 | 8/1995 | Hornung et al. | |
| 5,447,656 | * 9/1995 | Jungbauer et al. | 252/299.01 |
| 5,529,718 | * 6/1996 | Hornung et al. | 252/299.61 |
| 5,630,962 | * 5/1997 | Schlosser et al. | 252/299.61 |
| 5,648,021 | * 7/1997 | Wingen et al. | 252/299.62 |
| 5,702,638 | * 12/1997 | Wingen et al. | 252/299.62 |
| 5,744,059 | * 4/1998 | Yamashita et al. | 252/299.61 |
| 5,776,363 | * 7/1998 | Hornung et al. | 252/299.01 |

OTHER PUBLICATIONS

English language abstract of EP 0,603,786 published Jun. 29, 1994.
English language abstract of DE 19500768 published Sep. 28, 1995.
English language abstract of WO 9211241 published Jul. 9, 1992.

* cited by examiner

*Primary Examiner*—C. H. Kelly
(74) *Attorney, Agent, or Firm*—Frommer Lawrence & Haug LLP

(57) ABSTRACT

A ferroelectric liquid crystal mixture having a negative value of $\Delta e$ and allowing a high speed response and a low voltage driving, as well as a liquid crystal display devise using the crystal mixture of the invention. The ferroelectric liquid crystal mixture according to the invention comprises two or more compounds from at least two different of the following classes of compounds: A. thiadiazoles, B. phenanthrenes, C. 2-fluoropyridines, D. difluorobenzenes, E. meta-substituted aromatic compounds.

12 Claims, No Drawings

FERROELECTRIC LIQUID CRYSTAL MIXTURE

This application was filed as a Section 371 application of PCT application number EP 96/034154, filed Jul. 17, 1996.

The present invention relates to a novel ferroelectric liquid crystal mixture. More particularly, it relates to a ferroelectric liquid crystal mixture, which shows a high switching speed when driven at a low voltage, and a liquid crystal display device with the use of this liquid crystal mixture.

In these days, liquid crystal mixtures have been widely employed in practice as display devices of clocks, electronic calculators, small-sized television sets, etc. Among all, the most commonly employed products are those with the use of the nematic phase of liquid crystals and their display systems are called the twisted nematic (TN) type or the super twisted nematic (STN) type. However, the TN type is unsuitable for a display of a large information capacity, since its contrast is deteriorated with an increase in line number. Owing to the TFT driving system wherein each pixel is provided with a thin film transistor (TFT), the display characteristics of the TN type become more and more like those of a cathode ray tube (CRT) and thus the information capacity can be enlarged. However, its production process is highly complicated and achieves only a low yield, which results in an extremely high production cost. Moreover, it is scarcely applicable to a large screen.

Although the STN system, which is composed of a simple matrix, has improved display characteristics compared with the TN type, it is still insufficient when compared with the TFT-TN system. However, the STN system requires only a low production cost. Since Clark and Lagerwall found Surface Stabilized Ferroelectric Liquid Crystals (SSFLC) in 1980 [N. A. Clark and S. T. Lagerwall, Appl. Phys. Lett., 36, 899 (1980)], these liquid crystals have attracted attentions as display materials in the coming generation and a number of studies have been carried out thereon. The reasons therefor are as follows. (1) These ferroelectric liquid crystals have a high response speed. (2) They have memory properties which enable a display of a large information capacity and they can be produced at a relatively low cost, since no active device (thin film transistor, etc.) is needed. (3) They have a broad viewing angle. Thus, these liquid crystals are expected to be usable in a display device having a large screen size and a large display capacity.

To use a ferroelectric liquid crystal display device in practice, it is an important factor to achieve a highly defined contrast. It is very difficult to establish a highly defined contrast at the desired level by using ferroelectric liquid crystals. The reasons therefor reside in, for example, the zigzag defect in the smectic C phase, a decrease in the effective cone angle due to the chevron geometry, the insufficient memory properties, etc. There have been proposed various methods for achieving a highly defined contrast. Examples of these method include the use of an oblique vapor-deposition film as an alignment layer, the C1 uniform method by using an alignment layer having a high pretilt, the utilization of a quasi-bookshelf geometry through an AC electric field processing or by using a naphthalene-based compound, and the use of a material having a negative dielectric anisotropy. Among the above-mentioned methods, the one with the use of a material having a negative dielectric anisotropy ($\Delta\epsilon$) depends on a phenomenon that, when an electric field of a high frequency is applied perpendicularly to the electrode substrate, liquid crystal molecules having a negative $\Delta\epsilon$ are aligned in parallel with the electrode substrate. This phenomenon is called the AC stabilization effect.

Surguy [P. W. H. Surguy, et al., Ferroelectrics, 122, 63 (1991)] further proposed "a method with the use of a liquid crystal material having negative dielectric anisotropy". This method, which is largely accepted as a method for successfully achieving a highly defined contrast, is described in P. W. Ross, Proc. SID, 217, (1992).

A material with a negative dielectric anisotropy has a so called T–V characteristic, i.e., the pulse width (T) required for switching shows the minimum value (T–Vmin) with an increase in the voltage (V). Surguy et al. reported a driving system with the use of this characteristic. In this driving system, switching is effected under the voltage |Vs–Vd| but not under |Vs+Vd| or |Vd|.

The driving voltage in this system is determined by (T–Vmin) characteristics for the materials. According to Surguy et al., the value Vmin is defined as follows.

$$V_{min} = E_{min}*d = P_s*d/\sqrt{3}*\epsilon_0*\Delta\epsilon*\sin^2\theta.$$

In the above formula, Emin stands for the minimum strength of the electric field; d stands for the cell gap, Ps stands for the spontaneous polarization; $\Delta\epsilon$ stands for the dielectric anisotropy; and $\theta$ stands for the tilt angle of the liquid crystal material.

By taking the biaxial anisotropy ($\delta\epsilon$) into consideration, furthermore, Towler et al. obtained the values Vmin and Tmin as defined below.

$$|V_{min}| = \frac{P_s \cdot D}{\epsilon_0 \sqrt{3(\sin^2\theta - \partial\epsilon)}}$$

$$\tau_{min} \propto \frac{\eta(\Delta\epsilon\sin^2\theta - \partial\epsilon)}{P_s^2}$$

($\eta$: viscosity)
[M. J. Towel et al., Liquid Crystal, 11 (1992)].

However, the ferroelectric liquid crystal material disclosed by Ross et al. still shows only a slow response speed and [Vs+Vd] exceeds 55 V, which makes it less usable in practice. Accordingly, it has been required to develop a liquid crystal material which has a sufficiently large absolute value of the negative dielectric anisotropy, a large spontaneous polarization and a low viscosity. Ferroelectric liquid crystal mixtures appropriate for driving systems with the use of the AC stabilization effect or driving systems with the use of the T–Vmin characteristics are disclosed, e.g. in JP A 168792/1989, 306493/1989 and 4290/1992, JP B 29990/1995 and JP A 503444/1990.

However, since the development of ferroelectric liquid-crystal mixture in particular can in no way be regarded as complete, the manufactures of displays are still interested in a very wide variety of mixtures. Another reason for this is that only the interaction of the liquid-crystalline mixtures with the individual components of the display device or of the cells (for example the alignment layer) allows conclusions to be drawn on the quality of the liquid-crystalline mixtures too.

The object of the present invention was therefore to provide liquid crystalline mixtures which are suitable for improving the property profile of liquid crystal displays, particulary ferroelectric liquid crystal displays and especially ferroelectric liquid crystal (FLC) displays operated in the inverse mode.

A further object of the present invention is to provide a ferroelectric liquid crystal mixture, which has a negative value of Δε and is capable of achieving a high response speed and a low voltage driving, and a liquid crystal display device with the use of this liquid crystal mixture.

The present invention provides a ferroelectric liquid crystal mixture comprising at least two compounds selected from at least two different of the following groups of compounds:

A. (1,3,4)-thiadiazole derivatives of the formula (I),

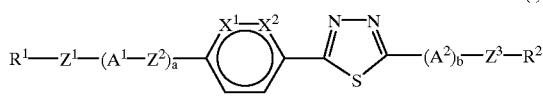

(I)

wherein the symbols and indices have the following meanings:

$R^1$ and $R^2$ independently of one another, are
(a) a hydrogen atom,
(b) a straight-chain or branched-chain alkyl group, with or without an asymmetric carbon atom, having from 2 to 16 carbon atoms, in which one or two, preferably non-adjacent, —$CH_2$— groups may be replaced by —O—, —S—, —CO—, —CO—O—, —O—CO—, —CH=CH—, —C≡C—, —Si($CH_3$)$_2$—, 1,4-cyclohexylene, 1,4-phenylene, cyclopropane-1,2-diyl or —O—CO—O—, with the proviso that —O— and/or —S— atoms must not be directly bonded to one another; one or more hydrogen atoms of the alkyl group may be substituted by F, Cl, CN and/or $CF_3$; or
(c) any one of the following chiral groups:

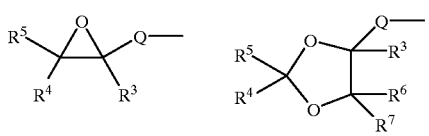

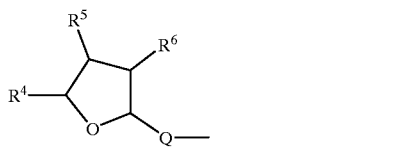

wherein $R^3$, $R^4$, $R^5$, $R^6$ and $R^7$, independently of one another, are a straight-chain or branched-chain alkyl group having from 1 to 16 carbon atoms (with or without an asymmetrical carbon atom), where one or more —$CH_2$— groups may also be replaced by —O— or —CH=CH—, with the proviso that oxygen atoms must not be bonded directly to one another; one or more hydrogen atoms of the alkyl group may be substituted with —F or —Cl; or $R^4$ and $R^5$ may also together be —($CH_2$)$_4$— or —($CH_2$)$_5$— if they are bonded to an oxirane, dioxolane or tetrahydrofuran system;

Q is —$CH_2$—O—, —CO—O— or a single bond;

$Z^1$, $Z^2$ and $Z^3$ independently of one another, are a single bond, —O—, —CO—O— or —O—CO—; with the proviso that, when $R^1$ is (c), then $Z^1$ is not a single bond, and that, when $R^2$ is (c), then $Z^2$ is not a single bond;

$A^1$ and $A^2$ are identical or different and are 1,4-phenylene, in which one or more H atoms may be replaced by F, pyridine-2,5-diyl, in which one H atom may be replaced by F, pyrimidine-2,5-diyl or trans-1,4-cyclohexylene;

a and b are 0 or 1 and a+b is 0 or 1;

$X^1$ and $X^2$ independently of one another, are —N—, —CF— or —CH—;

B. Phenanthrene derivatives of the formula (II)

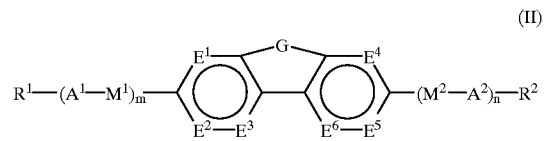

(II)

in which the symbols and indices have the following meanings:

$E^1$, $E^2$, $E^3$, $E^4$, $E^5$ and $E^6$ are —N—, —CF— or —CH—, with the following provisos:
if $E^1$ ($E^4$) is —N— or —CF—, $E^2$ and $E^3$ ($E^5$ and $E^6$) must be —CH—;
if $E^2$ and/or $E^3$ ($E^5$ and/or $E^6$) are —CF—, $E^1$ ($E^4$) must be —CH—;
if $E^2$ ($E^5$) is —N—, $E^1$ ($E^4$) must be —CH—, while $E^3$ ($E^6$) can be —CH— or —CF—; and
at least one of $E^1$ to $E^6$ must be —N— or —CF—;

G is —$CH_2CH_2$— or —CH=CH—;

$R^1$ and $R^2$, independently of one another, are hydrogen or a straight-chain or branched-chain alkyl group having from 1 to 20 carbon atoms (with or without an asymmetrical carbon atom), in which one or more —$CH_2$— groups may be replaced by —O—, —CO—O—, —O—CO—, —O—CO—O—, —CH=CH—, —C≡C—, cyclopropane-1,2-diyl, —Si($CH_3$)$_2$—, 1,4-phenylene, trans-1,4-cyclohexylene or trans-1,3-cyclopentylene, with the proviso that oxygen atoms and/or sulfur atoms must not be bonded directly to one another; one or more hydrogen atoms of the alkyl group may be substituted by —F, —Cl, —Br, —$CF_3$, —CN or —$OR^3$; or $R^1$, $R^2$ are one of the following chiral groups:

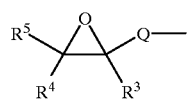 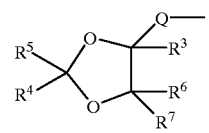

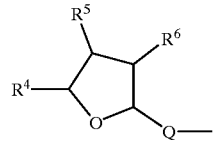

wherein $R^3$, $R^4$, $R^5$, $R^6$ and $R^7$, independently of one another, are a straight-chain or branched-chain alkyl group having from 1 to 16 carbon atoms (with or without an asymmetric carbon atom), where one or more —$CH_2$— groups may also be replaced by —O— or —CH=CH—, with the proviso that oxygen atoms must not be bonded directly to one another; one or more hydrogen atoms of the alkyl group may be substituted by —F or —Cl; or $R^4$ and $R^5$ may also together be —($CH_2$)$_4$— or —($CH_2$)$_5$— if they are bonded to an oxirane, dioxolane or tetrahydrofuran system;

Q is —$CH_2$—O—, —CO—O— or a single bond;

$M^1$ and $M^2$, independently of one another, are —CO—O—, —O—CO—, —$CH_2$—O—, —O—$CH_2$—, —$CH_2$—$CH_2$—, —C≡C— or a single bond;

A¹ and A², independently of one another, are 1,4-phenylene in which one or more hydrogen atoms may be substituted by F, Cl and/or CN, pyrazine-2,5-diyl pyridazine-3,6-diyl, pyridine-2,5-diyl in which one or more hydrogen atoms may be substituted with F, pyrimidine-2,5-diyl, trans-1,4-cyclohexylene in which one or two hydrogen atoms may be substituted with CN and/or $CH_3$;

n and m are 0 or 1, and the sum of n+m is 0 or 1.

C. 2-Fluoropyridine derivatives of the formula (III),

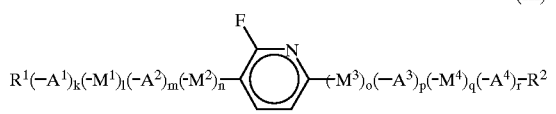

(III)

in which the symbols and indices have the following meanings:

$R^1$ and $R^2$, independently of one another, are hydrogen or a straight-chain or branched-chain alkyl group having from 1 to 16 carbon atoms (with or without an asymmetrical carbon atom), in which one or two non-adjacent —$CH_2$— groups may be replaced by —O—, —CO—, —CO—O—, —O—CO—, —O—CO—O—, —CH=CH—, —C≡C—, cyclopropane-1,2-diyl or —Si($CH_3$)$_2$—; one or more hydrogen atoms of the alkyl group may be substituted by F, Cl, CN and/or $CF_3$; or $R^1$, $R^2$ are one of the following chiral groups:

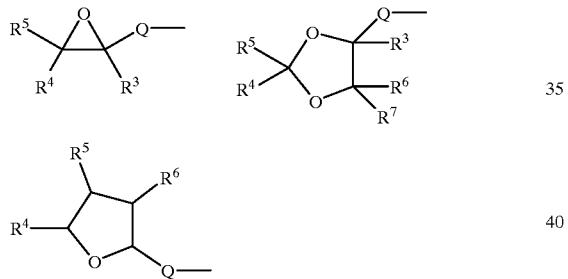

wherein $R^3$, $R^4$, $R^5$, $R^6$ and $R^7$, independently of one another, are a straight-chain or branched-chain alkyl group having from 1 to 16 carbon atoms (with or without an asymmetrical carbon atom), where one or more —$CH_2$— groups may also be replaced by —O— or —CH=CH—, with the proviso that oxygen atoms must not be bonded directly to one another; one or more hydrogen atoms of the alkyl group may be substituted by —F or —Cl; or $R^4$ and $R^5$ may also together be —($CH_2$)$_4$— or —($CH_2$)$_5$— if they are bonded to an oxirane, dioxolane or tetrahydrofuran system;

Q is —$CH_2$—O—, —CO—O— or a single bond;

$A^1$, $A^2$, $A^3$ and $A^4$, independently of one another, are 1,4-phenylene in which one or two hydrogen atoms may be substituted by F, or pyrazine-2,5-diyl, pyridazine-3,6-diyl, pyridine-2,5-diyl or pyrimidine-2,5-diyl, trans-1,4-cyclohexylene in which one or two hydrogen atoms may be substituted by CN, or naphthalene-2,6-diyl;

$M^1$, $M^2$, $M^3$ and $M^4$, independently of one another, are —O—, —S—, —CO—, —CO—O—, —O—CO—, —O—CO—O—, —$CH_2$—O—, —O—$CH_2$—, —$CH_2$—$CH_2$—, —CH=CH— or —C≡C— with the proviso that two M groups must not be bonded directly to one another; k, l, m, n, o, p, q and r are 0 or 1, with the proviso that the sum of k+m+p+r is more than 0 and less than 4, preferably less than 3;

D. Phenylene derivatives of the formula (IV),

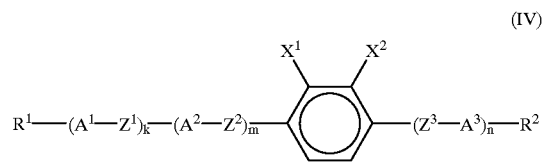

(IV)

wherein $R^1$ and $R^2$, independently of one another, are hydrogen or a straight-chain or branched-chain alkyl group having from 1 to 16 carbon atoms (with or without an asymmetrical carbon atom), in which one or two non-adjacent —$CH_2$— groups may be replaced by —O—, —CO—, —CO—O—, —O—CO—, —O—CO—O—, —CH=CH—, —C≡C—, cyclopropane-1,2-diyl, 1,4-phenylene, 1,4-cyclohexylene or —Si($CH_3$)$_2$—; and one or more hydrogen atoms of the alkyl group may be substituted by F, Cl, CN and/or $CF_3$; or $R^1$, $R^2$ are one of the following chiral groups:

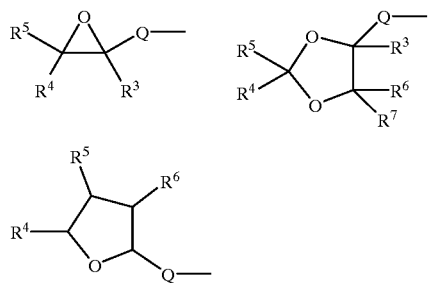

wherein $R^3$, $R^4$, $R^5$, $R^6$ and $R^7$, independently of one another, are a straight-chain or branched-chain alkyl group having from 1 to 16 carbon atoms (with or without an asymmetrical carbon atom), where one or more —$CH_2$— groups may also be replaced by —O— or —CH=CH—, with the proviso that oxygen atoms must not be bonded directly to one another; one or more hydrogen atoms of the alkyl group may be substituted by —F or —Cl; or $R^4$ and $R^5$ may also together be —($CH_2$)$_4$— or —($CH_2$)$_5$— if they are bonded to an oxirane, dioxolane or tetrahydrofuran system;

Q is —$CH_2$—O—, —CO—O— or a single bond;

$A^1$, $A^2$, $A^3$ are, independently of one another, 1,4-phenylene in which one or two H-atoms may be substituted by F, pyridin-2,5-diyl, pyrimidin-2,5-diyl, pyrazine-2,5-diyl, pyridazin-3,6-diyl, naphthalene-2,6-diyl, 1,2,3,4-tetrahydronapthalene-2,6-diyl or 1,4-cyclohexylene in which one or two hydrogen atoms may be substituted by CN and/or $CH_3$ groups;

$X^1$ and $X^2$ are selected from hydrogen, F, Cl, $CF_3$ and CN; with the proviso that $X^1$ and $X^2$ are not simultaneously hydrogen, preferably $X^1$ and $X^2$ are identical, particularly preferably $X^1$ and $X^2$ are both F;

each of $Z^1$ and $Z^2$ are —CO—O—, —O—CO—, —$CH_2CH_2$—, —O—$CH_2$—, —$CH_2$—O—, —C≡C— or a single bond;

each k, m and n are 0, 1 or 2, and (k+m+n) is 1 or 2; and

E. Meta-substituted aromatic compounds of the formula (V):

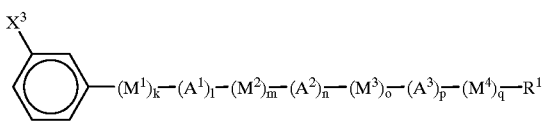

wherein $X^3$ is F, Cl, Br, CN, $CF_3$ or an straight chain or branched alkyl group having from 1 to 12 carbon atoms, in which one or two $CH_2$-groups may be replaced by —O—, —CO—O— or —O—CO—, and in which one or more hydrogen atoms in the alkyl group may be substituted by F, Cl or CN;

$R^1$ is hydrogen or a straight-chain or branched-chain alkyl group having from 1 to 16 carbon atoms (with or without asymmetrical carbon atoms), in which one or more hydrogen atoms may be substituted with F, Cl, CN and/or $CF_3$;

$A^1$, $A^2$ and $A^3$, independently of one another, are 1,4-phenylene in which one or two hydrogen atoms may be substituted by F, or pyrazine-2,5-diyl, pyridazine-3,6-diyl, pyridine-2,5-diyl or pyrimidine-2,5-diyl, trans-1,4-cyclohexylene in which one or two hydrogen atoms may be substituted by CN, or 1,3,4-thiadiazole-2,5-diyl, 1,3-dioxane-2,5-diyl, naphthalene-2,6-diyl, or 1,3-thiazole-2,4(5)-diyl;

$M^1$, $M^2$, $M^3$ and $M^4$, independently of one another, are —O—, —S—, —CO—, —CO—O—, —O—CO—, —O—CO—O—, —$CH_2$—O—, —O—$CH_2$—, —$CH_2$—$CH_2$—, —CH=CH— or —C≡C—, with the proviso that two M groups must not be bonded directly to one another;

k, l, m, n, o, p and q are 0 or 1, with the proviso that the sum of l+n+p is more than 0 and less than 4, preferably less than 3.

Preferred are those compounds of group A, in which the symbols and indices in the formula (I) have the following meanings:

$R^1$ and $R^2$ independently of one another, are
(a) a hydrogen atom,
(b) a straight-chain or branched-chain alkyl group, with or without an asymmetrical carbon atom, having from 2 to 16 carbon atoms, in which one or two non-adjacent —$CH_2$— groups may be replaced by —O—, —CO—O—, —O—CO—, —Si($CH_3$)$_2$—, 1,4-cyclohexylene or cyclopropane-1,2-diyl; one or more hydrogen atoms of the alkyl group may be substituted by F;

$Z^1$, $Z^2$ and $Z^3$ independently of one another, are a single bond, —CO—O— or —O—CO—; with the proviso that, when $R^1$ is (c), then $Z^1$ is not a single bond, and that, when $R_2$ is (c), then $Z_2$ is not a single bond;

$A^1$ and $A^2$ are identical or different and are 1,4-phenylene, in which one or more H atoms may be replaced by F, pyridine-2,5-diyl, in which one H atom may be replaced by F, pyrimidine-2,5-diyl, trans-1,4-cyclohexylene; a and b are 0 or 1 and a+b is 0 or 1;

$X^1$ and $X^2$ independently of one another, are —N—, —CF— or —CH—;

Examples of particularly preferred compounds of the formula (I) include:

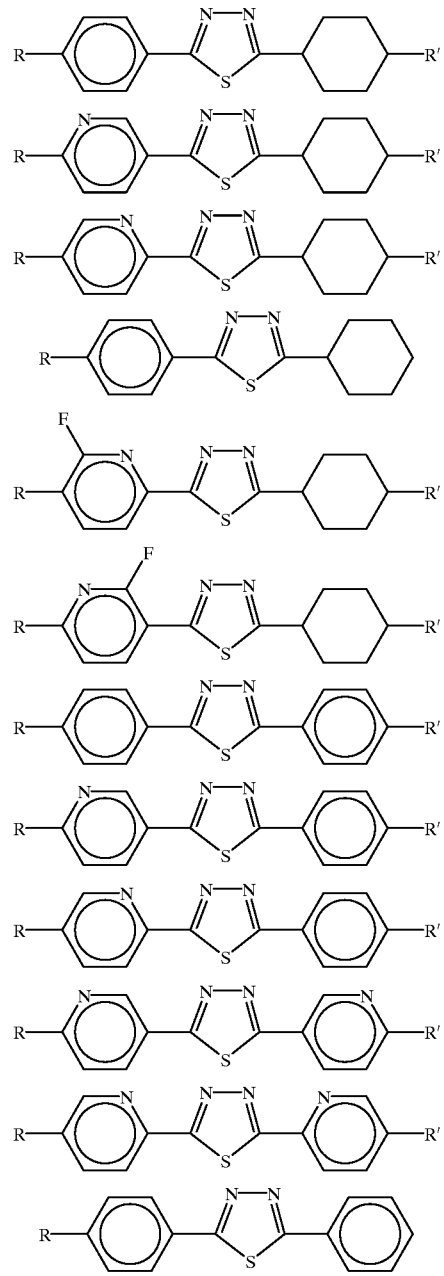

wherein R and R' have the same meanings as $R^1$ and $R^2$ in formula (I).

It is preferable in the present invention that a compound of the formula (I) itself has a smectic C phase. Accordingly, in the formula (I), at least one of R and R' is preferably an alkyl group having from 8 to 16 carbon atoms, more preferably a straight-chain alkyl group.

Preference is given to the compounds of the formula (I) in which $R^1$ and $R^2$ are a straight-chain or branched-chain alkyl group having from 1 to 16 carbon atoms (with or without an asymmetrical carbon atom), in which one or more —$CH_2$— groups may also be replaced by —O—, cyclopropane-1,2-diyl or —Si($CH_3$)$_2$—, with the proviso that oxygen atoms must not be bonded directly to one another; one or more hydrogen atoms of the alkyl group may be substituted by F; R or R' can also be hydrogen, but not both simultaneously.

Preference is given to the compounds of group B, i.e. of the formula (II), in which $R^1$ and $R^2$ are independently, a straight-chain or branched-chain alkyl group having from 1 to 10 carbon atoms, wherein a —CH$_2$— group separated from the ring by at least two further —CH$_2$— groups can also be replaced by —Si(CH$_3$)$_2$—.

Further preference is given to the compounds of the formula (IIa) in which E$^1$ and/or E$^4$ is —N—:

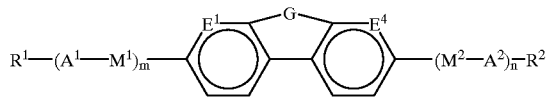

(IIa)

and of these, very particular preference is given to the following compounds (in all preferred compounds R$^1$ and R$^2$ have the same meaning as in formula (III):

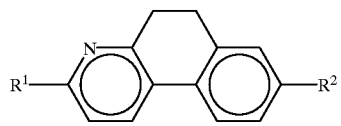

(IIa1)

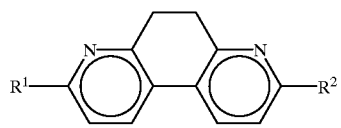

(IIa2)

(IIa3)

(IIa4)

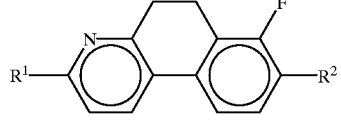

(IIa5)

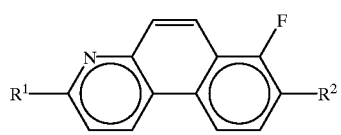

(IIa6)

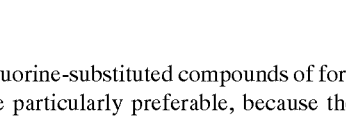

The fluorine-substituted compounds of formulae (Ia5) and (Ia6) are particularly preferable, because they have a large negative value of Δε.

Preference is furthermore given to the compounds of the formula (IIb) in which E$^2$ and/or E$^5$ are —N—:

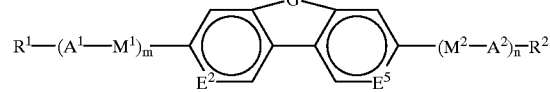

(IIb)

and of these, very particular preference is given to the following compounds:

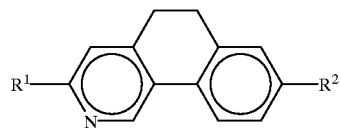

(IIb1)

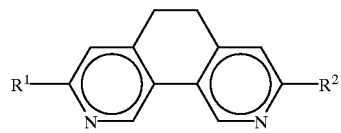

(IIb2)

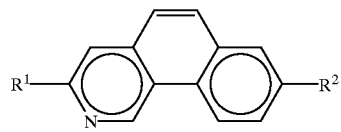

(IIb3)

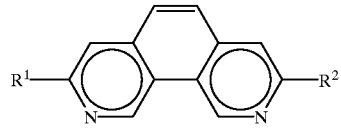

(IIb4)

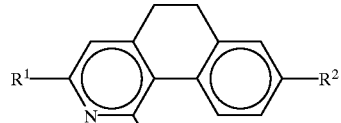

(IIb5)

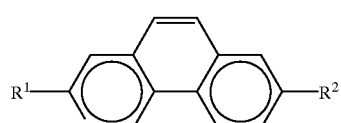

(IIb6)

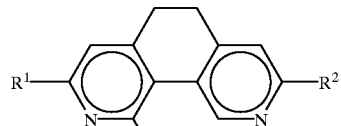

(IIb7)

(IIb8) 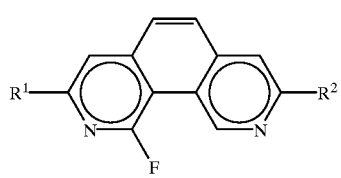

(IIb9) 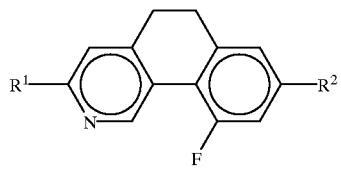

(IIb10) 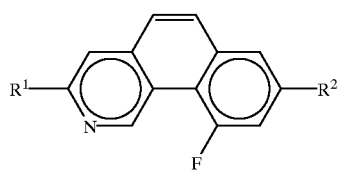

(IIb11) 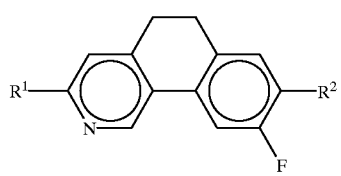

(IIb12) 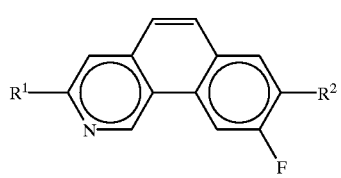

(IIb13) 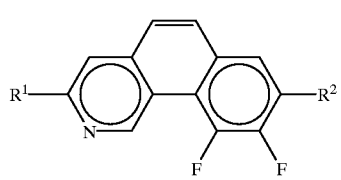

(IIb14) 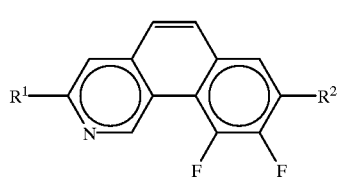

(IIb15) 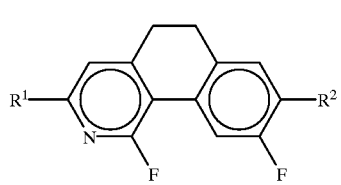

(IIb16) 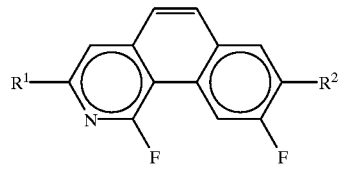

The fluorine-substituted compounds of formulae (Ib5) and (Ib6) are particularly preferable, because they have a large negative value of $\Delta\epsilon$.

Preference is given to the compounds of the formula (Ic) in which $E^1$ and/or $E^4$ are —CF—:

(IIc) 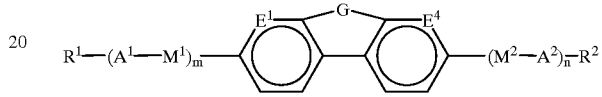

and of these, very particular preference is given to the following compounds:

(IIc1) 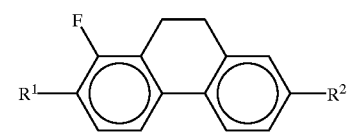

(IIc2) 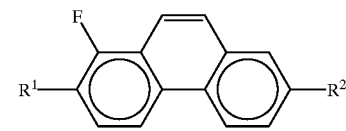

(IIc3) 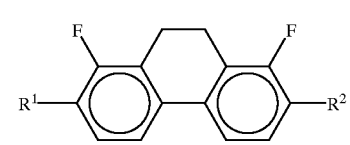

(IIc4) 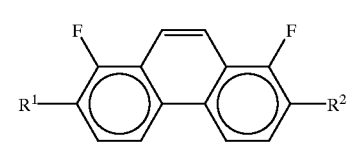

(IIc5) 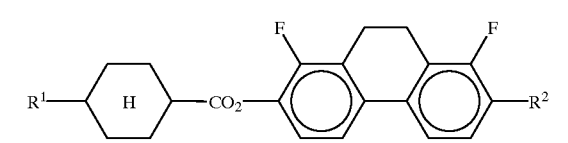

(IIc6) 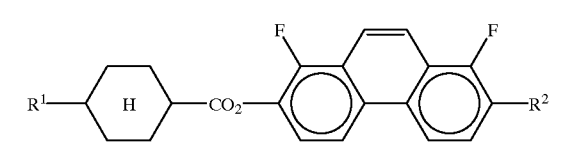

Preference is furthermore given to compounds of the formula (IId) in which $E^1$ and/or $E^4$ is —CH—, and $E^2$, $E^3$, $E^5$ and $E^6$ are —CH— or —CF—, and at least one of those is —CF—:

(IId)

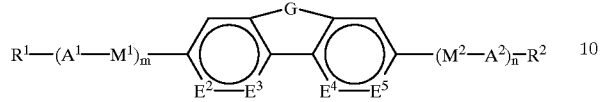

and of these, very particular preference is given to the following compounds:

(IId1)

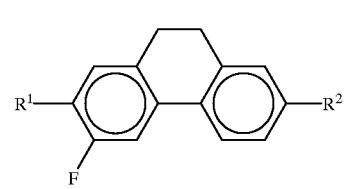

(IId2)

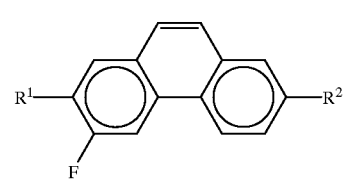

(IId3)

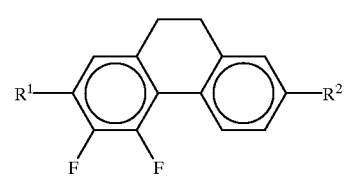

(IId4)

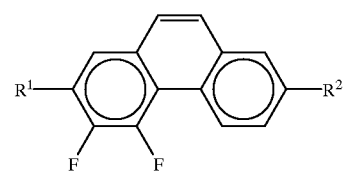

(IId5)

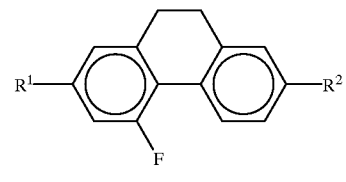

(IId6)

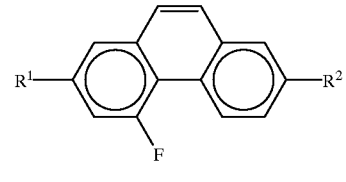

(IId7)

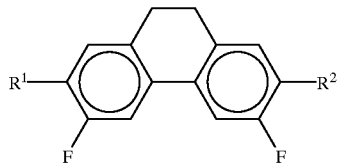

(IId8)

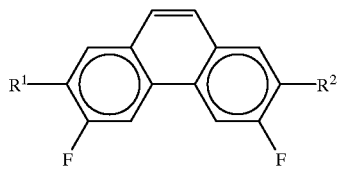

(IId9)

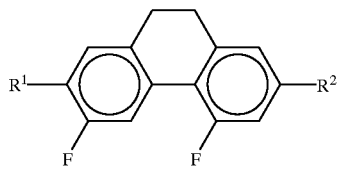

(IId10)

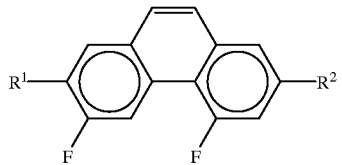

(IId11)

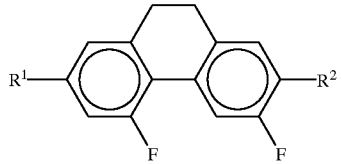

(IId12)

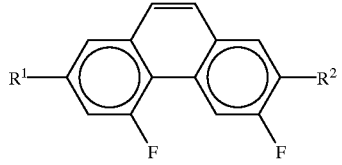

(IId13)

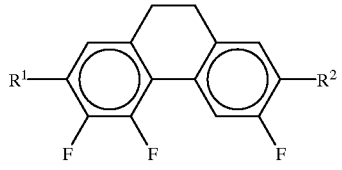

(IId14)

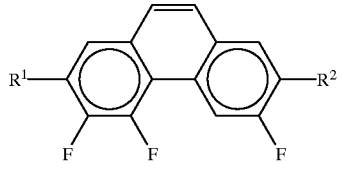

Examples of the particularly preferable compounds of the formula (2) include 1,8-difluoro-2,7-dioctyloxyphenanthrene, 1,8-difluoro-2,7-dibutoxyphenanthrene, 1,8-difluoro-2,7- dipentoxyphenanthrene, 1,8-difluoro- 2,7-dihexyloxyphenanthrene, 1,8-difluoro-2,7-diheptyloxyphenanthrene, 1,8-difluoro-2,7-dinonyloxyphenanthrene, 1,8-difluoro-2,7-didecyloxyphenanthrene, 1,8-difluoro-2,7-diundecyloxyphenanthrene, 1,8-difluoro-2,7-didodecyloxyphenanthrene, 1,8-difluoro-2-butoxy-7-pentoxyphenanthrene, 1,8-difluoro-2-butoxy-7-hexyloxyphenanthrene, 1,8-difluoro-2-butoxy-7-heptyloxyphenanthrene, 1,8-difluoro-2-butoxy-7-octyloxyphenanthrene, 1,8-difluoro-2-butoxy-7-nonyloxyphenanthrene, 1,8-difluoro-2-pentoxy-7-propoxyphenanthrene, 1,8-difluoro-2-pentoxy-7-hexyloxyphenanthrene, 1,8-difluoro-2-pentoxy-7-heptyloxyphenanthrene, 1,8-difluoro-2-pentoxy-7-octyloxyphenanthrene, 1,8-difluoro-2-pentoxy-7-nonyloxyphenanthrene, 1,8-difluoro-2-hexyloxy-7-propoxyphenanthrene, 1,8-difluoro-2-hexyloxy-7-heptyloxyphenanthrene, 1,8-difluoro-2-hexyloxy-7-octyloxyphenanthrene, 1,8-difluoro-2-hexyloxy-7-nonyloxyphenanthrene, 1,8-difluoro-2-hexyloxy-7-decyloxyphenanthrene, 1,8-difluoro-2-hexyloxy-7-dodecyloxyphenanthrene, 1,8-difluoro-2-heptyloxy-7-propoxyphenanthrene, 1,8-difluoro-2-heptyloxy-7-octyloxyphenanthrene, 1,8-difluoro-2-heptyloxy-7-nonyloxyphenanthrene, 1,8-difluoro-2-octyloxy-7-ethoxyphenanthrene, 1,8-difluoro-2-octyloxy-7-propoxyphenanthrene, 1,8-difluoro-2-octyloxy-7-nonyloxyphenanthrene, 1,8-difluoro-2-octyloxy-7-decyloxyphenanthrene, 1,8-difluoro-2-nonyloxy-7-ethoxyphenanthrene, 1,8-difluoro-2-nonyloxy-7-propoxyphenanthrene, 1,8-difluoro-2-nonyloxy-7-decyloxyphenanthrene, 1,8-difluoro-2-decyloxy-7-methoxyphenanthrene, 1,8-difluoro-2-decyloxy-7-ethoxyphenanthrene, 1,8-difluoro-2-decyloxy-7-propoxyphenanthrene, 1,8-difluoro-2-decyloxy-7-butoxyphenanthrene, 1,8-difluoro-2-decyloxy-7-pentoxyphenanthrene, 1,8-difluoro-2-decyloxy-7-heptyloxyphenanthrene, 1-fluoro-2,7-dibutoxyphenanthrene, 1-fluoro-2,7-dipentoxyphenanthrene, 1-fluoro-2,7-dihexyloxyphenanthrene, 1-fluoro-2,7-diheptyloxyphenanthrene, 1-fluoro-2,7-dioctyloxyphenanthrene, 1-fluoro-2,7-dinonyloxyphenanthrene, 1-fluoro-2,7-didecyloxyphenanthrene, 1-fluoro-2,7-diundecyloxyphenanthrene, 1-fluoro-2,7-didodecyloxyphenanthrene, 1-fluoro-2-butoxy-7-pentoxyphenanthrene, 1-fluoro-2-butoxy-7-hexyloxyphenanthrene, 1-fluoro-2-butoxy-7-heptyloxyphenanthrene, 1-fluoro-2-butoxy-7-octyloxyphenanthrene, 1-fluoro-2-butoxy-7-nonyloxyphenanthrene, 1-fluoro-2-butoxy-7-decyloxyphenanthrene, 1-fluoro-2-pentoxy-7-hexyloxyphenanthrene, 1-fluoro-2-pentoxy-7-heptyloxyphenanthrene, 1-fluoro-2-pentoxy-7-octyloxyphenanthrene, 1-fluoro-2-pentoxy-7-nonyloxyphenanthrene, 1-fluoro-2-hexyloxy-7-butoxyphenanthrene, 1-fluoro-2-hexyloxy-7-pentoxyphenanthrene, 1-fluoro-2-hexyloxy-7-heptyloxyphenanthrene, 1-fluoro-2-hexyloxy-7-octyloxyphenanthrene, 1-fluoro-2-hexyloxy-7-nonyloxyphenanthrene, 1-fluoro-2-hexyloxy-7-decyloxyphenanthrene, 1-fluoro-2-heptyloxy-7-propoxyphenanthrene, 1-fluoro-2-heptyloxy-7-butoxyphenanthrene, 1-fluoro-2-heptyloxy-7-pentoxyphenanthrene, 1-fluoro-2-heptyloxy-7-octyloxyphenanthrene, 1-fluoro-2-heptyloxy-7-nonyloxyphenanthrene, 1-fluoro-2-heptyloxy-7-decyloxyphenanthrene, 1-fluoro-2-octyloxy-phenanthrene, 1-fluoro-2-octyloxy-7-propoxyphenanthrene, 1-fluoro-2-octyloxy-7-butoxyphenanthrene, 1-fluoro-2-octyloxy-7-pentoxyphenanthrene, 1-fluoro-2-octyloxy-7-hexyloxyphenanthrene, 1-fluoro-2-octyloxy-7-octyloxyphenanthrene, 1-fluoro-2-octyloxy-7-nonyloxyphenanthrene, 1-fluoro-2-octyloxy-7-decyloxyphenanthrene, 1-fluoro-2-octyloxy-7-undecyloxyphenanthrene, 1-fluoro-2-nonyloxy-7-propoxyphenanthrene, 1-fluoro-2-nonyloxy-7-butoxyphenanthrene, 1-fluoro-2-nonyloxy-7-pentuxyphenanthrene, 1-fluoro-2-nonyloxy-7-hexyloxyphenanthrene, 1-fluoro-2-nonyloxy-7-heptyloxyphenanthrene, 1-fluoro-2-nonyloxy-7-octyloxyphenanthrene, 1-fluoro-2-nonyloxy-7-decyloxyphenanthrene, 2,7-bis(hexyloxy)-1,8-diazaphenanthrene, 2,7-bis(pentoxy)-1,8-diazaphenanthrene, 2,7-bis(heptyloxy)-1,8-diazaphenanthrene, 2,7-bis(octyloxy)-1,8-diazaphenanthrene, 2,7-bis(nonyloxy)-1,8-diazaphenanthrene, 2,7-bis(decyloxy)-1,8-diazaphenanthrene, 2,7-bis(undecyloxy)-1,8-diazaphenanthrene, 2,7-bis(dodecyloxy)-1,8-diazaphenanthrene, 2-butoxy-7-pentoxy-1,8-diazaphenanthrene, 2-butoxy-7-hexyloxy-1,8-diazaphenanthrene, 2-butoxy-7-heptyloxy-1,8-diazaphenanthrene, 2-butoxy-7-octyloxy-1,8-diazaphenanthrene, 2-butoxy-7-nonyloxy-1,8-diazaphenanthrene, 2-butoxy-7-decyloxy-1,8-diazaphenanthrene, 2-pentoxy-7-hexyloxy-1,8-diazaphenanthrene, 2-pentoxy-7-heptyloxy-1,8-diazaphenanthrene, 2-pentoxy-7-octyloxy- 1,8-diazaphenanthrene, 2-pentoxy-7-nonyloxy-1,8-diazaphenanthrene, 2-pentoxy-7-decyloxy-1,8-diazaphenanthrene, 2-hexyloxy-7-heptyloxy-1,8-diazaphenanthrene, 2-hexyl oxy-7-octyloxy-1,8-diazaphenanthrene, 2-hexyloxy-7-nonyloxy-1,8-diazaphenanthrene, 2-hexyloxy-7-decyloxy-1,8-diazaphenanthrene, 2-hexyloxy-7-(4-butyldimethylsilyl)butoxy-1,8-diazaphenanthrene, 2-hexyloxy-1,8-diazaphenanthrene, 2-hexyloxy-7-methyl-1,8-diazaphenanthrene, 2-heptyl oxy-7-octyloxy-1,8-diazaphenanthrene, 2-heptyloxy-7-nonyloxy-1,8-diazaphenanthrene, 2-heptyloxy-7-decyloxy-1,8-diazaphenanthrene, 2-heptyloxy-7-(6-methyl)octyloxy-1,8-diazaphenanthrene, 2-octyloxy-7-nonyloxy-1,8-diazaphenanthrene, 2-octyloxy-7-decyloxy-1,8-diazaphenanthrene, 2-octyloxy-7-undecyloxy-1,8-diazaphenanthrene, 2-octyloxy-7-dodecyloxy-1,8-diazaphenanthrene, 2-octyloxy-7-(5-oxa)nonyloxy-1,8-diazaphenanthrene, 2-nonyloxy-7-decyloxy-1,8-diazaphenanthrene, 2-nonyloxy-7-undecyloxy-1,8-diazaphenanthrene, 2-nonyloxy-7-dodecyloxy-1,8-diazaphenanthrene, 2-decyloxy-7-undecyloxy-1,8-diazaphenanthrene, 2-decyloxy-7-dodecyloxy-1,8-diazaphenanthrene, 2-butoxy-7-pentoxy-1-azaphenanthrene, 2-butoxy-7-hexyloxy-1-azaphenanthrene, 2-butoxy-7-heptyloxy-1-azaphenanthrene, 2-butoxy-7-octyloxy-1-azaphenanthrene, 2-butoxy-7-nonyloxy-1-azaphenanthrene, 2-butoxy-7-decyloxy-1-azaphenanthrene, 2-pentoxy-7-hexyloxy-1-azaphenanthrene, 2-pentoxy-7-heptyloxy-1-azaphenanthrene, 2-pentoxy-7-octyloxy-1-azaphenanthrene, 2-pentoxy-7-nonyloxy-1-azaphenanthrene, 2-pentoxy-7-decyloxy-1-azaphenanthrene, 2-hexyloxy-7-heptyloxy-1- azaphenanthrene, 2-hexyloxy-7-octyloxy-1-azaphenanthrene, 2-hexyloxy-7-nonyloxy-1-azaphenanthrene, 2-hexyloxy-7-decyloxy-1-azaphenanthrene, 2-hexyloxy-7-(4-butyldimethylsilyl)butoxy-1-azaphenanthrene, 2-heptyloxy-7-octyloxy-1-azaphenanthrene, 2-heptyloxy-7-nonyloxy-1-azaphenanthrene, 2-heptyloxy-7-decyloxy-1-azaphenanthrene, 2-heptyloxy-7-(6-methyl)octyloxy-1-azaphenanthrene, 2-octyloxy-7-nonyloxy-1-azaphenanthrene, 2-octyloxy-7-decyloxy-1-azaphenanthrene, 2-octyloxy-7-undecyloxy-1-azaphenanthrene, 2-octyloxy-7-dodecyloxy-1-azaphenanthrene, 2-octyloxy-7-(5-oxa)nonyloxy-1-azaphenanthrene, 2-nonyloxy-7-decyloxy-1-azaphenanthrene, 2-nonyloxy-7-undecyloxy-1-azaphenanthrene, 2-nonyloxy-7-dodecyloxy-1-azaphenanthrene, 2-decyloxy-7-undecyloxy-1-azaphenanthrene, 2-decyloxy-7-dodecyloxy-1-azaphenanthrene, 2-hexyloxy-7-pentoxy-1-azaphenanthrene, 2-heptyloxy-7-hexyloxy-1-azaphenanthrene, 2-heptyloxy-7-pentoxy-1-azaphenanthrene, 2-octyloxy-7-butoxy-1-azaphenanthrene, 2-octyloxy-7-pentoxy-1-azaphenanthrene, 2-octyloxy-7-hexyloxy-1-azaphenanthrene, 2-octyloxy-7-heptyloxy-1-azaphenanthrene, 2-nonyloxy-7-pentoxy-1-azaphenanthrene, 2-nonyloxy-7-hexyloxy-1-azaphenanthrene, 2-nonyloxy-7-heptyloxy-1-azaphenanthrene, 2-nonyloxy-7-octyloxy-1-azaphenanthrene, 2-butoxy-7-pentoxy-8-fluoro-1-azaphenanthrene, 2-butoxy-7-hexyloxy-8-fluoro-1-azaphenanthrene, 2-butoxy-7-heptyloxy-8-fluoro-1-azaphenanthrene, 2-butoxy-7-octyloxy-8-fluoro-1-azaphenanthrene, 2-butoxy-7-nonyloxy-8-fluoro-1-azaphenanthrene, 2-butoxy-7-decyloxy-8-fluoro-1-azaphenanthrene, 2-pentoxy-7-hexyloxy-8-fluoro-1-azaphenanthrene, 2-pentoxy-7-heptyloxy-8-fluoro-1-azaphenanthrene, 2-pentoxy-7-octyloxy-8-fluoro-1-azaphenanthrene, 2-pentoxy-7-nonyloxy-8-fluoro-1-azaphenanthrene, 2-pentoxy-7-decyloxy-8-fluoro-1-azaphenanthrene, 2-hexyloxy-7-heptyloxy-8-fluoro-1-azaphenanthrene, 2,7-bis(hexyloxy)-8-fluoro-1-azaphenanthrene, 2-hexyloxy-7-octyloxy-8-fluoro-1-azaphenanthrene, 2-hexyloxy-7-nonyloxy-8-fluoro-1-azaphenanthrene, 2-hexyloxy-7-decyloxy-8-fluoro-1-azaphenanthrene, 2-hexyloxy-7-(4-butyldimethylsilyl)butoxy-8-fluoro-1-azaphenanthrene, 2-heptyloxy-7-octyloxy-8-fluoro-1-azaphenanthrene, 2-heptyloxy-7-nonyloxy-8-fluoro-1-azaphenanthrene, 2-heptyloxy-7-decyloxy-8-fluoro-1-azaphenanthrene, 2-heptyloxy-7-(6-methyl)octyloxy-8-fluoro-1-azaphenanthrene, 2-octyloxy-7-nonyloxy-8-fluoro-1-azaphenanthrene, 2-octyloxy-7-decyloxy-8-fluoro-1-azaphenanthrene, 2-octyloxy-7-undecyloxy-8-fluoro-1-azaphenanthrene, 2-octyloxy-7-dodecyloxy-8-fluoro-1-azaphenanthrene, 2-octyloxy-7-(5-oxa)nonyloxy-8-fluoro-1-azaphenanthrene, 2-nonyloxy-7-decyloxy-8-fluoro-1-azaphenanthrene, 2-nonyloxy-7-undecyloxy-8-fluoro-1-azaphenanthrene, 2-nonyloxy-7-dodecyloxy-8-fluoro-1-azaphenanthrene, 2-decyloxy-7-undecyloxy-8-fluoro-1-azaphenanthrene, 2-decyloxy-7-dodecyloxy-8-fluoro- 1-azaphenanthrene, 2-hexyloxy-7-pentoxy-8-fluoro-1-azaphenanthrene, 2-heptyloxy-7-hexyl-8-fluoro-1-azaphenanthrene, 2-heptyloxy-7-pentoxy-8-fluoro-1-azaphenanthrene, 2-octyloxy-7-butoxy-8-fluoro-1-azaphenanthrene, 2-octyloxy-7-pentoxy-8-fluoro-1-azaphenanthrene, 2-octyloxy-7-hexyloxy-8-fluoro-1-azaphenanthrene, 2-octyloxy-7-heptyloxy-8-fluoro-1-azaphenanthrene, 2-nonyloxy-7-pentoxy-8-fluoro-1-azaphenanthrene, 2-nonyloxy-7-hexyloxy-8-fluoro-1-azaphenanthrene, 2-nonyloxy-7-heptyloxy-8-fluoro-1-azaphenanthrene, 2-nonyloxy-7-octyloxy-8-fluoro-1-azaphenanthrene, 2-hexyloxy-8-fluoro-1-azaphenanthrene, 1,8-difluoro-2,7-dioctyloxy-9,10-dihydrophenanthrene, 1,8-difluoro-2,7-dibutoxy-9,10-dihydrophenanthrene, 1,8-difluoro-2,7-dipentoxy-9,10-dihydrophenanthrene, 1,8-difluoro-2,7-dihexyloxy-9,10-dihydrophenanthrene, 1,8-difluoro-2,7-diheptyloxy-9,10-dihydrophenanthrene, 1,8-difluoro-2,7-dinonyloxy-9,10-dihydrophenanthrene, 1,8-difluoro-2,7-didecyloxy-9,10-dihydrophenanthrene, 1,8-difluoro-2,7-diundecyloxy-9,10-dihydrophenanthrene, 1,8-difluoro-2,7-didodecyloxy-9,10-dihydrophenanthrene, 1,8-difluoro-2-butoxy-7-pentoxy-9,10-dihydrophenanthrene, 1,8-difluoro-2-butoxy-7-hexyloxy-9,10-dihydrophenanthrene, 1,8-difluoro-2-butoxy-7-heptyloxy-9,10-dihydrophenanthrene, 1,8-difluoro-2-butoxy-7-octyloxy-9,10-dihydrophenanthrene, 1,8-difluoro-2-butoxy-7-nonyloxy-9,10-dihydrophenanthrene, 1,8-difluoro-2-pentoxy-7-propoxy-9,10-dihydrophenanthrene, 1,8-difluoro-2-pentoxy-7-hexyloxy-9,10-dihydrophenanthrene, 1,8-difluoro-2-pentoxy-7-heptyloxy-9,10-dihydrophenanthrene, 1,8-difluoro-2-pentoxy-7-octyloxy-9,10-dihydrophenanthrene, 1,8-difluoro-2-pentoxy-7-nonyloxy-9,10-dihydrophenanthrene, 1,8-difluoro-2-hexyloxy-7-propoxy-9,10-dihydrophenanthrene, 1,8-difluoro-2-hexyloxy-7-heptyloxy-9,10-dihydrophenanthrene, 1,8-difluoro-2-hexyloxy-7-octyloxy-9,10-dihydrophenanthrene, 1,8-difluoro-2-hexyloxy-7-nonyloxy-9,10-dihydrophenanthrene, 1,8-difluoro-2-hexyloxy-7-decyloxy-9,10-dihydrophenanthrene, 1,8-difluoro-2-hexyloxy-7-dodecyloxy-9,10-dihydrophenanthrene, 1,8-difluoro-2-heptyloxy-7-propoxy-9,10-dihydrophenanthrene, 1,8-difluoro-2-heptyloxy-7-octyloxy-9,10-dihydrophenanthrene, 1,8-difluoro-2-heptyloxy-7-nonyloxy-9,10-dihydrophenanthrene, 1,8-difluoro-2-octyloxy-7-ethoxy-9,10-dihydrophenanthrene, 1,8-difluoro-2-octyloxy-7-propoxy-9,10-dihydrophenanthrene, 1,8-difluoro-2-octyloxy-7-nonyloxy-9,10-dihydrophenanthrene, 1,8-difluoro-2-octyloxy-7-decyloxy-9,10-dihydrophenanthrene, 1,8-difluoro-2-nonyloxy-7-ethoxy-9,10-dihydrophen-anthrene, 1,8-difluoro-2-nonyloxy-7-propoxy-9,10-dihydrophenanthrene, 1,8-difluoro-2-nonyloxy-7-decyloxy-9,10-dihydrophenanthrene, 1,8-difluoro-2-decyloxy-7-methoxy-9,10-dihydrophenanthrene, 1,8-difluoro-2-decyloxy-7-ethoxy-9,10-dihydrophenanthrene, 1,8-difluoro-2-decyloxy-7-propoxy-9,10-dihydrophenanthrene, 1,8-difluoro-2-decyloxy-7-butoxy-9,10-dihydrophenanthrene, 1,8-difluoro-2-decyloxy-7-pentoxy-9,10-dihydrophenanthrene, 1,8-difluoro-2-decyloxy-7-heptyloxy-9,10-dihydrophenanthrene, 1-fluoro-2,7-dibutoxy-9,10-dihydrophenanthrene, 1-fluoro-2,7-dipentoxy-9,10-dihydrophenanthrene, 1-fluoro-2,7-dihexyloxy-9,10-dihydrophenanthrene, 1-fluoro-2,7-diheptyloxy-9,10-dihydrophenanthrene, 1-fluoro-2,7-dioctyloxy-9,10-dihydrophenanthrene, 1-fluoro-2,7-dinonyloxy-9,10-dihydrophenanthrene, 1-fluoro-2,7-didecyloxy-9,10-dihydrophenanthrene, 1-fluoro-2,7-diundecyloxy-9,10-dihydrophenanthrene, 1-fluoro-2,7-didodecyloxy-9,10-dihydrophenanthrene, 1-fluoro-2-butoxy-7-pentoxy-9,10-dihydrophenanthrene, 1-fluoro-2-butoxy-7-hexyloxy-9,10-dihydrophenanthrene, 1-fluoro-2-butoxy-7-heptyloxy-9,10-dihydrophenanthrene, 1-fluoro-2-butoxy-7-octyloxy-9,10-dihydrophenanthrene, 1-fluoro-2-butoxy-7-nonyloxy-9,10-dihydrophenanthrene, 1-fluoro-2-butoxy-7-decyloxy-9,10-dihydrophenanthrene, 1-fluoro-2- pentoxy-7-hexyloxy-9,10-dihydrophenanthrene, 1-fluoro-2-pentoxy-7-heptyloxy-9,10-dihydrophenanthrene, 1-fluoro-2-pentoxy-7-octyloxy-9,10-dihydrophenanthrene, 1-fluoro-2-pentoxy-7-nonyloxy-9,10-dihydrophen-anthrene, 1-fluoro-2-hexyloxy-7-butoxy-9,10-dihydrophenanthrene, 1-fluoro-2-hexyloxy-7-pentyloxy-9,10-dihydrophenanthrene, 1-fluoro-2-hexyloxy-7-heptyloxy-9,10-dihydrophenanthrene, 1-fluoro-2-hexyloxy-7-octyloxy-9,10-dihydrophenanthrene, 1-fluoro-2-hexyloxy-7-nonyloxy-9,10-dihydrophenanthrene, 1-fluoro-2-hexyloxy-7-decyloxy-9,10-dihydrophenanthrene, 1-fluoro-2-heptyloxy-7-propoxy-9,10-dihydrophenanthrene, 1-fluoro-2-heptyloxy-7-butoxy-9,10-dihydrophenanthrene, 1-fluoro-2-heptyloxy-7-pentyloxy-9,10-dihydrophenanthrene, 1-fluoro-2-heptyloxy-7-octyloxy-9,10-dihydrophenanthrene, 1-fluoro-2-heptyloxy-7-nonyloxy-9,10-dihydrophenanthrene, 1-fluoro-2-heptyloxy-7-decyloxy-9,10-dihydrophenanthrene, 1-fluoro-2-octyloxy-7-propoxy-9,10-dihydrophenanthrene, 1-fluoro-2-octyloxy-7-butoxy-9,10-dihydrophenanthrene, 1-fluoro-2-octyloxy-7-pentyloxy-9,10-dihydrophenanthrene, 1-fluoro-2-octyloxy-7-hexyloxy-9,10-dihydrophinanthrene, 1-fluoro-2-octyloxy-7-octyloxy-9,10-dihydrophenanthrene, 1-fluoro-2-octyloxy-7-nonyloxy-9,10-dihydrophenanthrene, 1-fluoro-2-octyloxy-7-decyloxy-9,10-dihydrophenanthrene, 1-fluoro-2-octyloxy-7-undecyloxy-9,10-dihydrophenanthrene, 1-fluoro-2-nonyloxy-7-propoxy-9,10-dihydrophenanthrene, 1-fluoro-2-nonyloxy-7-butoxy-9,10-dihydrophenanthrene, 1-fluoro-2-nonyloxy-7-pentyloxy-9,10-dihydrophenanthrene, 1-fluoro-2-nonyloxy-7-hexyloxy-9,10-dihydrophenanthrene, 1-fluoro-2-nonyloxy-7-heptyloxy-9,10-dihydrophenanthrene, 1-fluoro-2-nonyloxy-7-octyloxy-9,10-dihydrophenanthrene, 1-fluoro-2-nonyloxy-7-decyloxy-9,10-dihydrophenanthrene, 2,7-bis(pentoxy)1,8-diaza-9,10-dihydrophenanthrene, 2,7-bis(heptyloxy)1,8-diaza-9,10-dihydrophenanthrene, 2,7-bis(octyloxy)1,8-diaza-9,10-dihydrophenanthrene, 2,7-bis(nonyloxy)1,8-diaza-9,10-dihydrophenanthrene, 2,7-bis(decyloxy)1,8-diaza-9,10-dihydrophenanthrene, 2,7-bis(undecyloxy)1,8-diaza-9,10-dihydrophenanthrene, 2,7-bis(dodecyloxy)1,8-diaza-9,10-dihydrophenanthrene, 2-butoxy-7-pentoxy-1,8-diaza-9,10-dihydrophenanthrene, 2-butoxy-7-hexyloxy-1,8-diaza-9,10-dihydrophenanthrene, 2-butoxy-7-heptyloxy-1,8-diaza-9,10-dihydrophenanthrene, 2-butoxy-7-octyloxy-1,8-diaza-9,10-dihydrophenanthrene, 2-butoxy-7-nonyloxy-1,8-diaza-9,10-dihydrophenanthrene, 2-butoxy-7-decyloxy-1,8-diaza-9,10-dihydrophenanthrene, 2-pentoxy-7-hexyloxy-1,8-diaza-9,10-dihydrophenanthrene, 2-pentoxy-7-heptyloxy-1,8-diaza-9,10-dihydrophenanthrene, 2-pentoxy-7-octyloxy-1,8-diaza-9,10-dihydrophenanthrene, 2-pentoxy-7-nonyloxy-1,8-diaza-9,10-dihydrophenanthrene, 2-pentoxy-7-decyloxy-1,8-diaza-9,10-dihydrophenanthrene, 2-hexyloxy-7-heptyloxy-1,8-diaza-9,10-dihydrophenanthrene, 2-hexyloxy-7-octyloxy-1,8-diaza-9,10-dihydrophenanthrene, 2-hexyloxy-7-nonyloxy- 1,8-diaza-9,10-dihydrophenanthrene, 2-hexyloxy-7-decyloxy-1,8-diaza-9,10-dihydrophenanthrene, 2-hexyloxy-7-(4-butyldimethylsilyl)butoxy-1,8-diaza-9,10-dihydrophenanthrene, 2-heptyloxy-7-octyloxy-1,8-diaza-9,10-dihydrophenanthrene, 2-heptyloxy-7-nonyloxy-1,8-diaza-9,10-dihydrophenanthrene, 2-heptyloxy-7-decyloxy-1,8-diaza-9,10-dihydrophenanthrene, 2-heptyloxy-7-(6-methyl)octyloxy-1,8-diaza-9,10-dihydrophenanthrene, 2-octyloxy-7-nonyloxy-1,8-diaza-9,10-dihydrophenanthrene, 2-octyloxy-7-decyloxy-1,8-diaza-9,10-dihydrophenanthrene, 2-octyloxy-7-undecyloxy-1,8-diaza-9,10-dihydrophenanthrene, 2-octyloxy-7-dodecyloxy-1,8-diaza-9,10-dihydrophenanthrene, 2-octyloxy-7-(5-oxa)nonyloxy-1,8-diaza-9,10-dihydrophenanthrene, 2-nonyloxy-7-decyloxy-1,8-diaza-9,10-dihydrophenanthrene, 2-nonyloxy-7-undecyloxy-1,8-diaza-9,10-dihydrophenanthrene, 2-nonyloxy-7-dodecyloxy-1,8-diaza-9,10-dihydrophenanthrene, 2-decyloxy-7-undecyloxy-1,8-diaza-9,10-dihydrophenanthrene, 2-decyloxy-7-dodecyloxy-1,8-diaza-9,10-dihydrophenanthrene, 2-butoxy-7-pentoxy-1-aza-9,10-dihydrophenanthrene, 2-butoxy-7-hexyloxy-1-aza-9,10-dihydrophenanthrene, 2-butoxy-7-heptyloxy-1-aza-9,10-dihydrophenanthrene, 2-butoxy-7-octyloxy-1-aza-9,10-dihydrophenanthrene, 2-butoxy-7-nonyloxy-1-aza-9,10-dihydrophenanthrene, 2-butoxy-7-decyloxy-1-aza-9,10-dihydrophenanthrene, 2-pentoxy-7-hexyloxy-1-aza-9,10-dihydrophenanthrene, 2-pentoxy-7-heptyloxy-1-aza-9,10-dihydrophenanthrene, 2-pentoxy-7-octyloxy-1-aza-9,10-dihydrophenanthrene, 2-pentoxy-7-nonyloxy-1-aza-9,10-dihydrophenanthrene, 2-pentoxy-7-decyloxy-1-aza-9,10-dihydrophenanthrene, 2-hexyloxy-7-heptyloxy-1-aza-9,10-dihydrophenanthrene, 2-hexyloxy-7-octyloxy-1-aza-9,10-dihydrophenanthrene, 2-hexyloxy-7-nonyloxy-1-aza-9,10-dihydrophenanthrene, 2-hexyloxy-7-decyloxy-1-aza-9,10-dihydrophenanthrene, 2-hexyloxy-7-(4-butyldimethylsilyl)butoxy-1-aza-9,10-dihydrophenanthrene, 2-heptyloxy-7-octyloxy-1-aza-9,10-dihydrophenanthrene, 2-heptyloxy-7-nonyloxy-1-aza-9,10-dihydrophenanthrene, 2-heptyloxy-7-decyloxy-1-aza-9,10-dihydrophenanthrene, 2-heptyloxy-7-(6-methyl)octyloxy-1-aza-9,10-dihydrophenanthrene, 2-octyloxy-7-nonyloxy-1-aza-9,10-dihydrophenanthrene, 2-octyloxy-7-decyloxy-1-aza-9,10-dihydrophenanthrene, 2-octyloxy- 7-undecyloxy-1-aza-9,10-dihydrophenanthrene, 2-octyloxy-7-dodecyloxy-1-aza-9,10-dihydrophenanthrene, 2-octyloxy-7-(5-oxa)nonyloxy-1-aza-9,10-dihydrophenanthrene, 2-nonyloxy-7-decyloxy-1-aza-9,10-dihydrophenanthrene, 2-nonyloxy-7-undecyloxy-1-aza-9,10-dihydrophenanthrene, 2-nonyloxy-7-dodecyloxy-1-aza-9,10-dihydrophenanthrene, 2-decyloxy-7-undecyloxy-1-aza-9,10-dihydrophenanthrene, 2-decyloxy-7-dodecyloxy-1-aza-9,10-dihydrophenanthrene, 2-hexyloxy-7-pentoxy-1-aza-9,10-dihydrophenanthrene, 2-heptyloxy-7-hexyloxy-1-aza-9,10-dihydrophenanthrene, 2-heptyloxy-7-pentoxy-1-aza-9,10-dihydrophenanthrene, 2-octyloxy-7-butoxy-1-aza-9,10-dihydrophenanthrene, 2-octyloxy-7-pentoxy-1-aza-9,10-dihydrophenanthrene, 2-octyloxy-7-hexyloxy-1-aza-9,10-dihydrophenanthrene, 2-octyloxy-7-heptyloxy-1-aza-9,10-dihydrophenanthrene, 2-nonyloxy-7-pentoxy-1-aza-9,10-dihydrophenanthrene, 2-nonyloxy-7-hexyloxy-1-aza-9,10-dihydrophenanthrene, 2-nonyloxy-7-heptyloxy-1-aza-9,10-dihydrophenanthrene, 2-nonyloxy-7-octyloxy-1-aza-9,10-dihydrophenanthrene, 2-butoxy-7-pentoxy-8-fluoro-1-aza-9,10-dihydrophenanthrene, 2-butoxy-7-hexyloxy-8-fluoro-1-aza-9,10-dihydrophenanthrene, 2-butoxy-7-heptyloxy-8-fluoro-1-aza-9,10-dihydrophenanthrene, 2-butoxy-7-octyloxy-8-fluoro-1-aza-9,10-dihydrophenanthrene, 2-butoxy-7-nonyloxy-8-fluoro-1-aza-9,10-dihydrophenanthrene, 2-butoxy-7-decyloxy-8-fluoro-1-aza-9,10-dihydrophenanthrene, 2-pentoxy-7-hexyloxy-8-fluoro-1-aza-9,10-dihydrophenanthrene, 2-pentoxy-7-heptyloxy-8-fluoro-1-aza-9,10-dihydrophenanthrene, 2-pentoxy-7-octyloxy-8-fluoro-1-aza-9,10-dihydrophenanthrene, 2-pentoxy-7-nonyloxy-8-fluoro-1-aza-9,10-dihydrophenanthrene, 2-pentoxy-7-decyloxy-8-fluoro-1-aza-9,10-dihydrophenanthrene, 2-hexyloxy-7-heptyloxy-8-fluoro-1-aza-9,10-dihydrophenanthrene, 2-hexyloxy-7- octyloxy-8-fluoro-1-aza-9,10-dihydrophenanthrene, 2-hexyloxy-7-nonyloxy-8-fluoro-1-aza-9,10-dihydrophenanthrene, 2-hexyloxy-7-decyloxy-8-fluoro-1-aza-9,10-dihydrophenanthrene, 2-hexyloxy-7-(4-butyldimethylsilyl)butoxy-8-fluoro-1-aza-9,10-dihydrophenanthrene, 2-heptyloxy-7-octyloxy-8-fluoro-1-aza-9,10-dihydrophenanthrene, 2-heptyloxy-7-nonyloxy-8-fluoro-1-aza-9,10-dihydrophenanthrene, 2-heptyloxy-7-decyloxy-8-fluoro-1-aza-9,10-dihydrophenanthrene, 2-heptyloxy- 7-(6-methyl)octyloxy-8-fluoro-1-aza-9,10-dihydrophenanthrene, 2-octyloxy-7-nonytoxy-8-fluoro-1-aza-9,10-dihydrophenanthrene, 2-octyloxy-7-decyloxy-8-fluoro-1-aza-9,10-dihydrophenanthrene, 2-octyloxy-7-undecyloxy-8-fluoro-1-aza-9,10-dihydrophenanthrene, 2-octyloxy-7-dodecyloxy-8-fluoro-1-aza-9,10-dihydrophenanthrene, 2-octyloxy-7-(5-oxa)nonyloxy-8-fluoro-1-aza-9,10-dihydrophenanthrene, 2-nonyloxy-7-decyloxy-8-fluoro-1-aza-9,10-dihydrophenanthrene, 2-nonyloxy-7-undecyloxy-8-fluoro-1-aza-9,10-dihydrophenanthrene, 2-nonyloxy-7-dodecyloxy-8-fluoro-1-aza-9,10-dihydrophenanthrene, 2-decyloxy-7-undecyloxy-8-fluoro-1-aza-9,10-dihydrophenanthrene, 2-decyloxy-7-dodecyloxy-8-fluoro-1-aza-9,10-dihydrophenanthrene, 2-hexyloxy-7-pentoxy-8-fluoro-1-aza-9,10-dihydrophenanthrene, 2-heptyloxy-7-hexyloxy-8-fluoro-1-aza-9,10-dihydrophenanthrene, 2-heptyloxy-7-pentoxy-8-fluoro-1-aza-9,10-dihydrophenanthrene, 2-octyloxy-7-butoxy-8-fluoro-1-aza-9,10-dihydrophenanthrene, 2-octyloxy-7-pentoxy-8-fluoro-1-aza-9,10-dihydrophenanthrene, 2-octyloxy-7-hexyloxy-8-fluoro-1-aza-9,10-dihydrophenanthrene, 2-octyloxy-7-heptyloxy-8-fluoro-1-aza-9,10-dihydrophenanthrene, 2-nonyloxy-7-pentoxy-8-fluoro-1-aza-9,10-dihydrophenanthrene, 2-nonyloxy-7-hexyloxy-8-fluoro-1-aza-9,10-dihydrophenanthrene, 2-nonyloxy-7-heptyloxy-8-fluoro-1-aza-9,10-dihydrophenanthrene, 2-nonyloxy-7-octyloxy-8-fluoro-1-aza-9, 10-dihydrophenanthrene, and 2-nonyloxy-7-octyloxy-8-fluoro-1-aza-9,10-dihydrophenanthrene.

Preferred compounds of component C., i.e. 2-fluoropyridine derivatives of the formula (III), are those in which the symbols and indices have the following meanings:

$R^1$ and $R^2$, independently of one another, are hydrogen or a straight-chain or branched-chain alkyl group having from 1 to 16 carbon atoms (with or without an asymmetrical carbon atom), in which one or two non-adjacent —CH$_2$— groups may be replaced by —O—, —CO—O—, —O—CO— or —Si(CH$_3$)$_2$—; one or more hydrogen atoms of the alkyl group may be substituted by F;

$A^1$, $A^2$, $A^3$ and $A^4$, independently of one another, are 1,4-phenylene in which one or two hydrogen atoms may be substituted by F, trans-1,4-cyclohexylene or naphthalene-2,6-diyl;

$M^1$, $M^2$, $M^3$ and $M^4$, independently of one another, are —CO—O—, —O—CO—, —CH$_2$—O— or —O—CH$_2$—;

k, l, m, n, o, p, q and r are 0 or 1, with the proviso that the sum of k+m+p+r is more than 0 and less than 4, preferably less than 3.

Particulary preferable compounds of the formula (III) include:

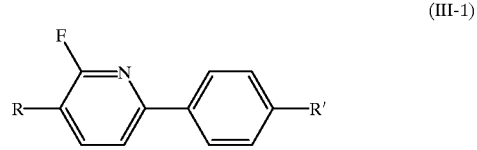

(III-1)

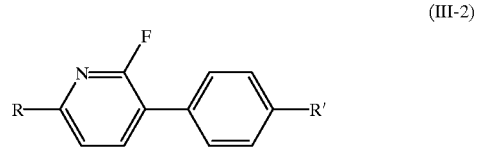

(III-2)

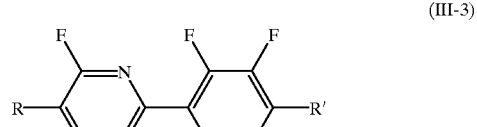

(III-3)

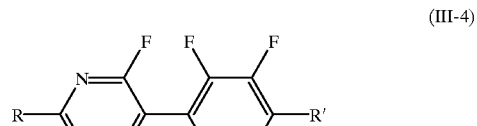

(III-4)

(III-5)

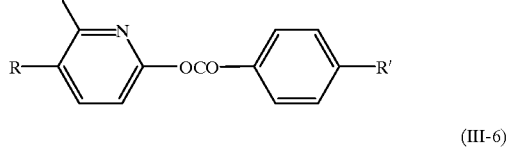

(III-6)

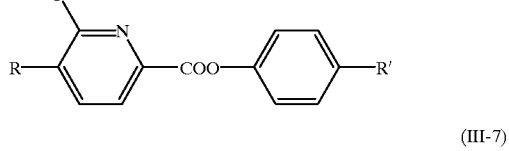

(III-7)

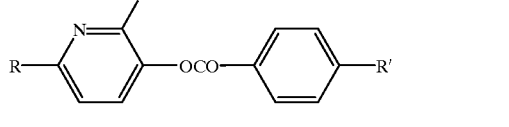

(III-8)

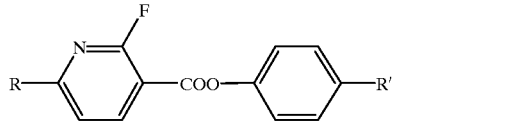

(III-9)

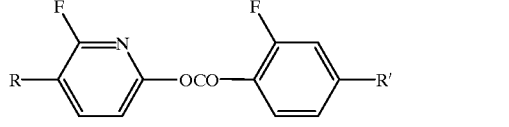

(III-10)

-continued
(III-11)
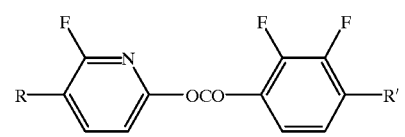
(III-12)
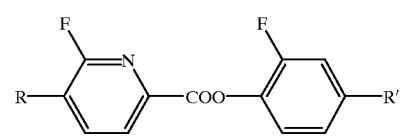
(III-13)
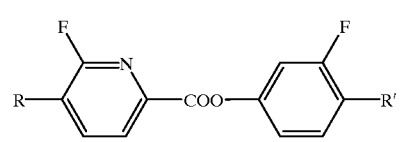
(III-14)
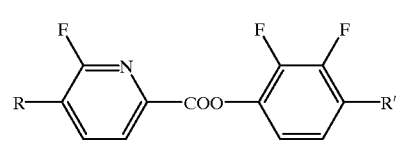
(III-15)
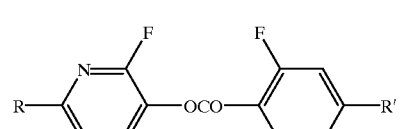
(III-16)
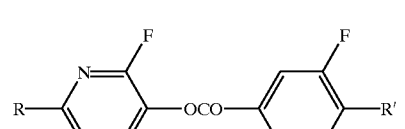
(III-17)
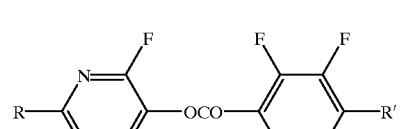
(III-18)
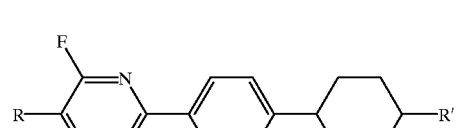
(III-19)
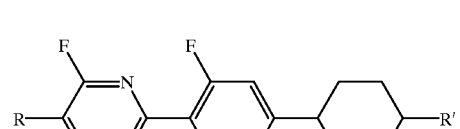
(III-20)
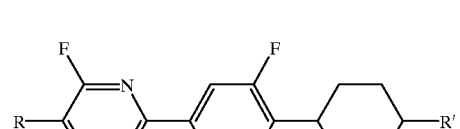
-continued
(III-21)
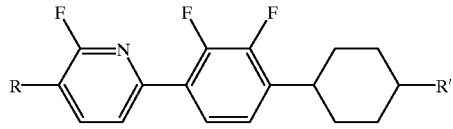
(III-22)
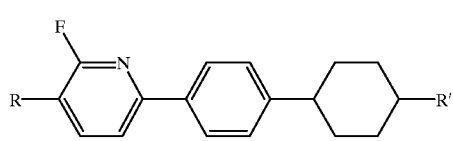
(III-23)
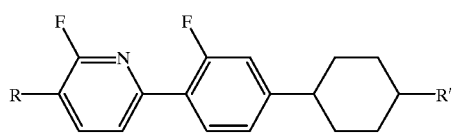
(III-24)
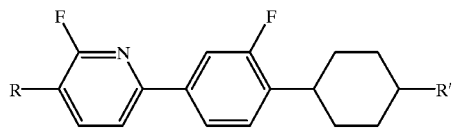
(III-25)
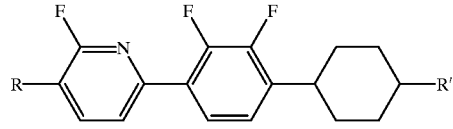
(III-26)
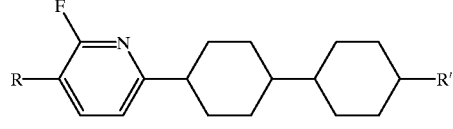
(III-27)
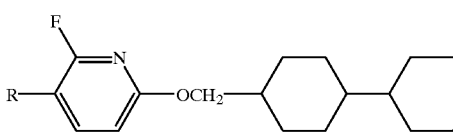
(III-28)
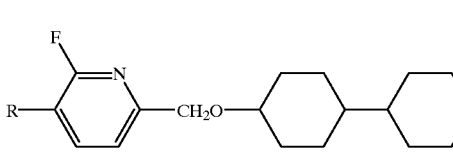
(III-29)
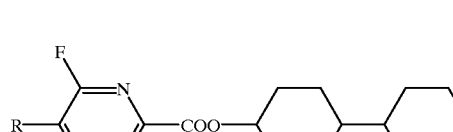
(III-30)
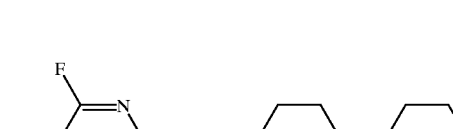

-continued
(III-31)
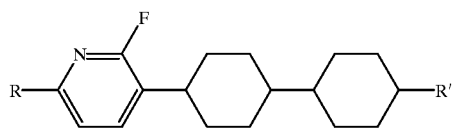
(III-32)
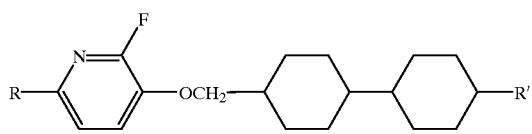
(III-33)
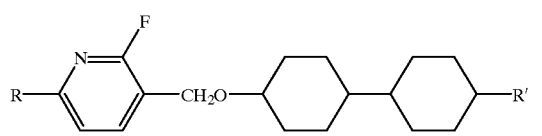
(III-34)
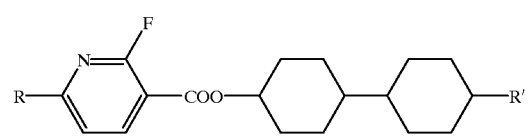
(III-35)
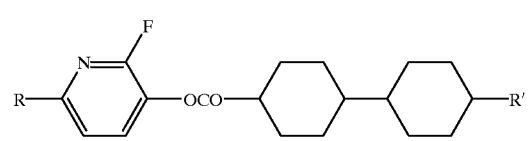
(III-36)
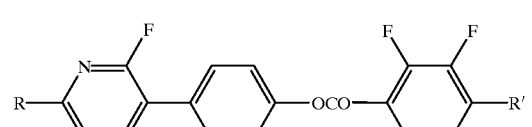
(III-37)
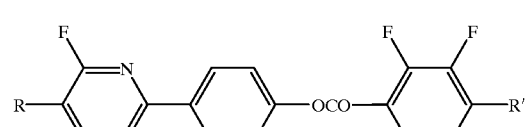
(III-38)
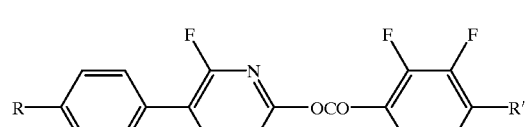
(III-39)
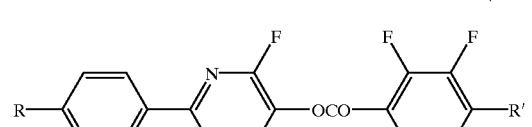
(III-40)
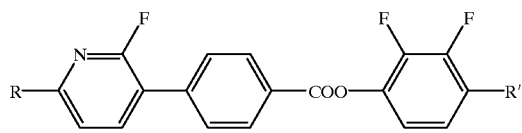
(III-41)
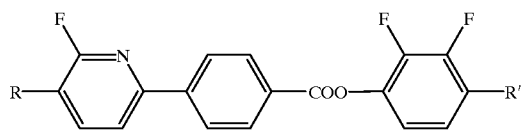
(III-42)
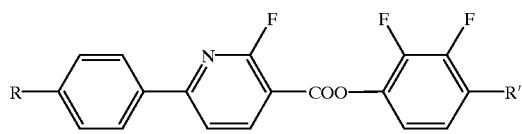
(III-43)
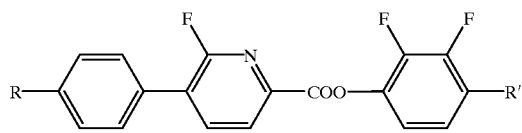
(III-44)
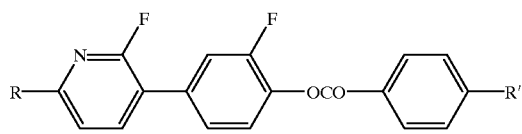
(III-45)
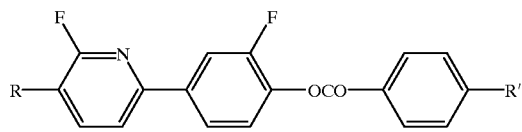
(III-46)
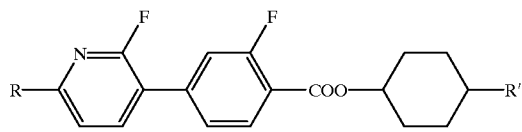
(III-47)
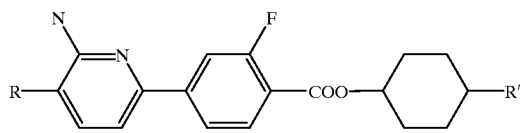
(III-48)
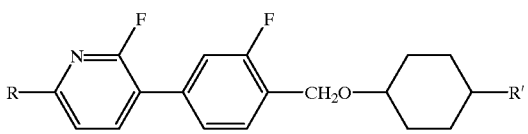

-continued

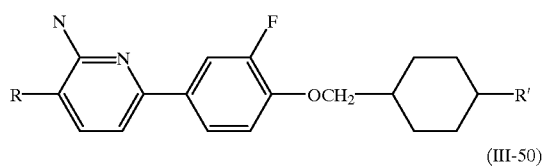
(III-49)

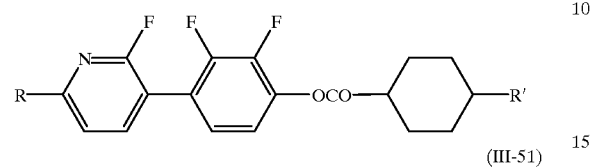
(III-50)

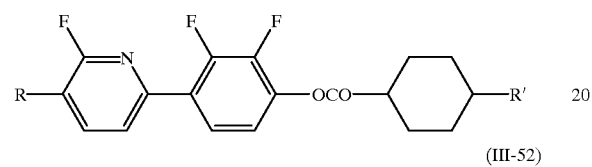
(III-51)

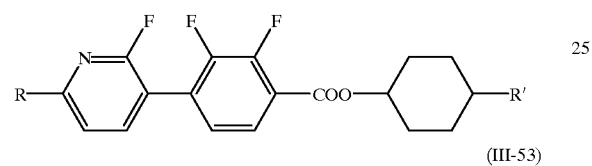
(III-52)

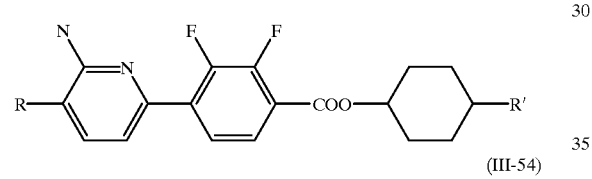
(III-53)

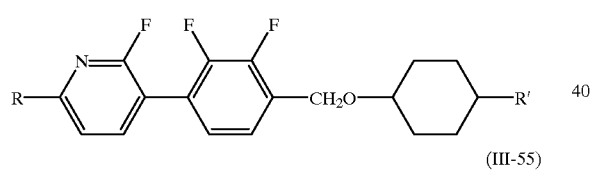
(III-54)

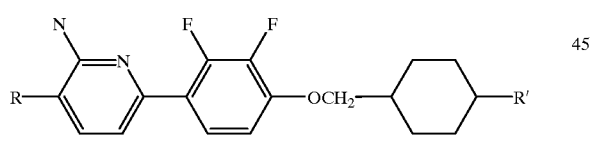
(III-55)

wherein R and R' have the same meanings as $R^1$ and $R^2$ in formula (III).

Preferred compounds of group D, i.e., of formula (IV), are those in which the symbols and indices in formula (IV) have the following meanings:

$R^1$ and $R^2$, independently of one another, are hydrogen or a straight-chain or branched-chain alkyl group having from 1 to 16 carbon atoms (with or without an asymmetrical carbon atom), in which one or two non-adjacent —CH$_2$— groups may be replaced by —O—, —CO—O—, —O—CO— or —Si(CH$_3$)$_2$—, and one or more hydrogen atoms of the alkyl group may be substituted by F;

$A^1$, $A^2$ and $A^3$, independently of one another, 1,4-phenylene in which one or two H atoms may be substituted by F, pyridin-2,5-diyl, pyrimidin-2,5-diyl, naphthalene-2,6-diyl or 1,4-cyclohexylene;

$X^1$ and $X^2$ are selected from hydrogen and F; with the proviso that $X^1$ and $X^2$ are not simultaneously hydrogen, preferably $X^1$ and $X^2$ are both F, each of $Z^1$ and $Z^2$ are —CO—O—, —O—CO—, —O—CH$_2$—, —CH$_2$—O—, —C≡C— or a single bond;

each k, m and n are 0, 1 or 2, and (k+m+n) is 1 or 2.

Examples of particularly preferred compounds of the formula (IV) include:

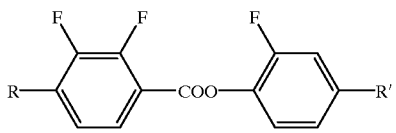
(IV-28)

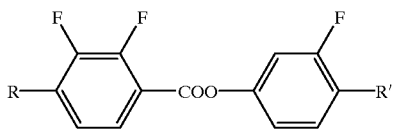
(IV-29)

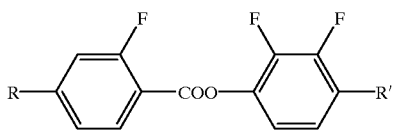
(IV-30)

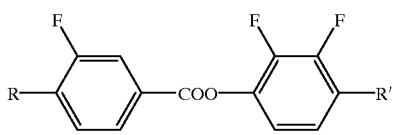
(IV-31)

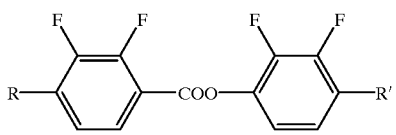
(IV-32)

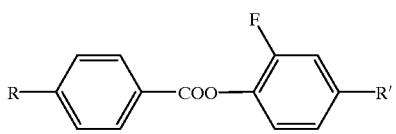
(IV-21)

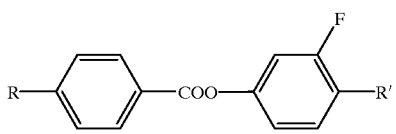
(IV-22)

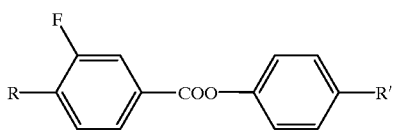
(IV-23)

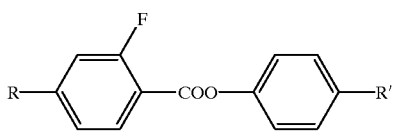
(IV-24)

(IV-25) 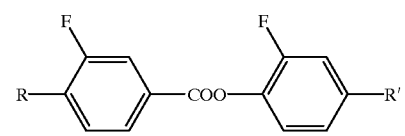
(IV-26) 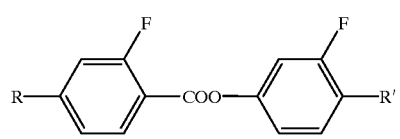
(IV-27) 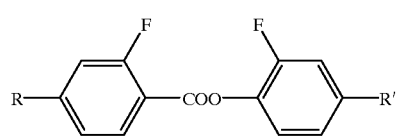
(IV-13) 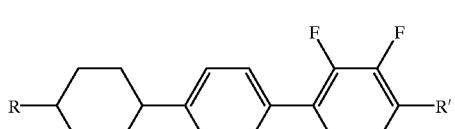
(IV-14) 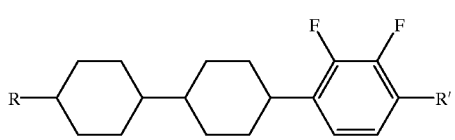
(IV-15) 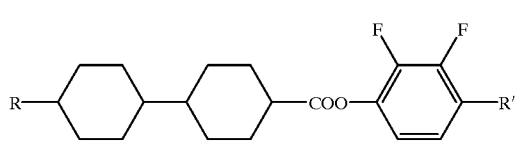
(IV-16) 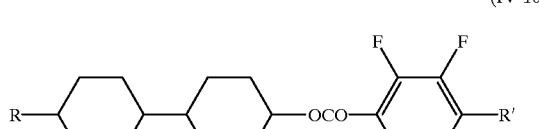
(IV-17) 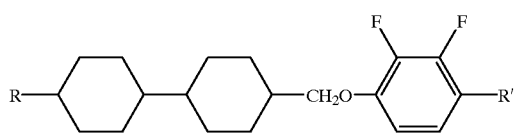
(IV-18) 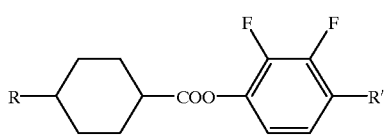
(IV-19) 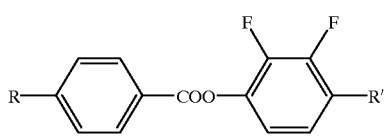
(IV-20) 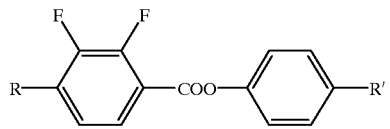
(IV-7) 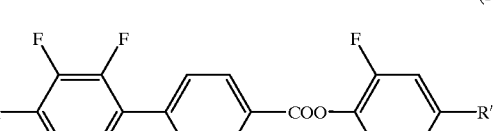
(IV-8) 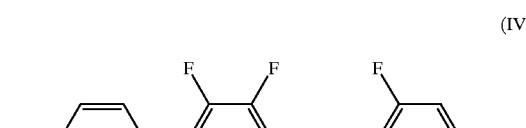
(IV-9) 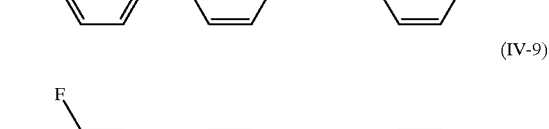
(IV-10) 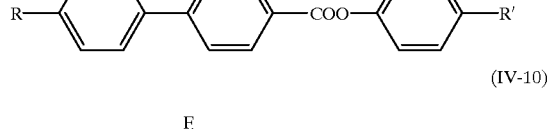
(IV-11) 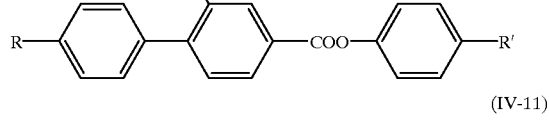
(IV-12) 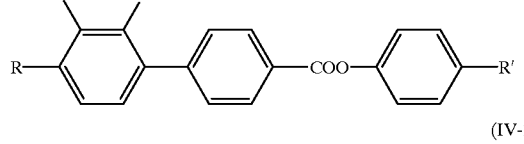
(IV-1) 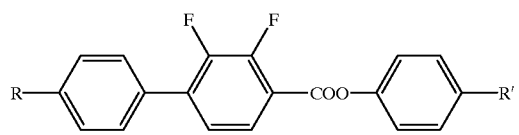
(IV-2) 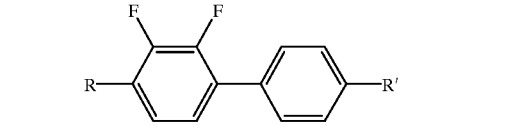
(IV-3) 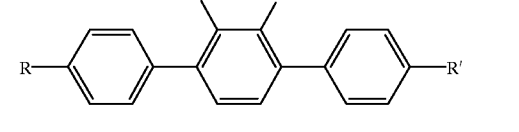

(IV-4)
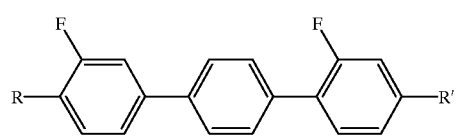
(IV-5)
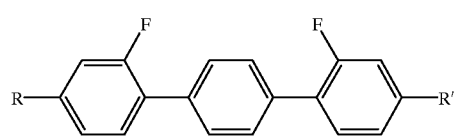
(IV-6)
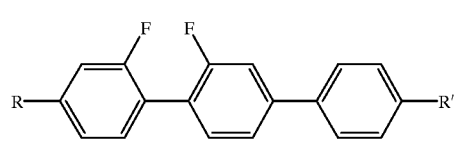
(IV-33)
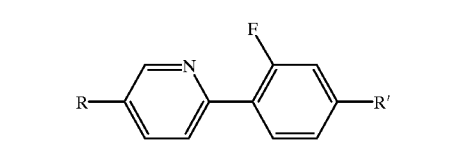
(IV-34)
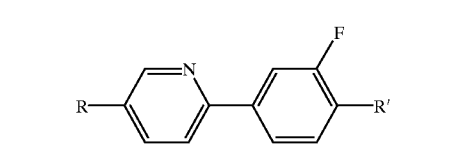
(IV-35)
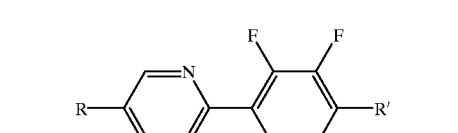
(IV-36)
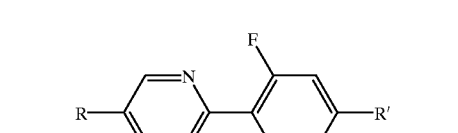
(IV-37)
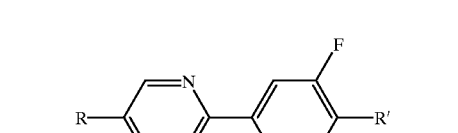
(IV-38)
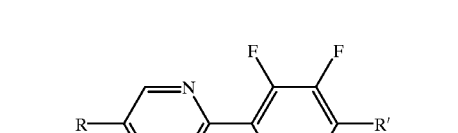
(IV-39)
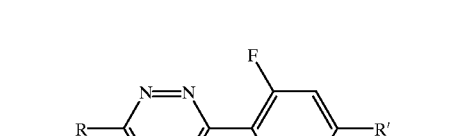
(IV-40)
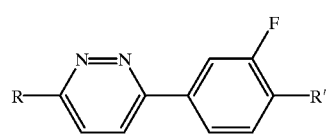
(IV-41)
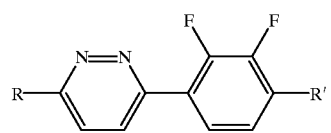
(IV-42)
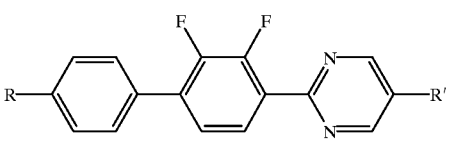
(IV-43)
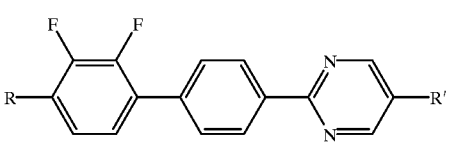
(IV-44)
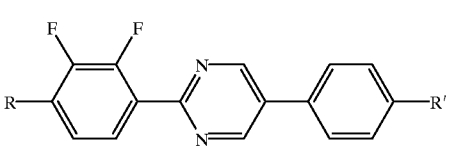
(IV-45)
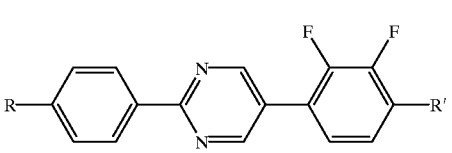
(IV-46)
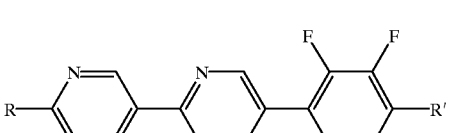
(IV-47)
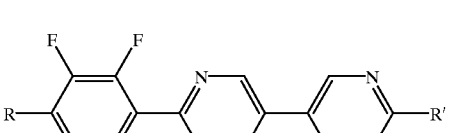
(IV-48)
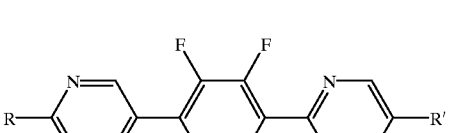
(IV-49)
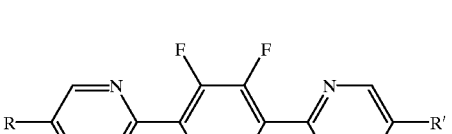

wherein R and R' have the same meaning as $R^1$ and $R^2$ in formula (IV).

Preferred compounds of group E, i.e. of formula (V), are those, in which the symbols and indices in the formula (V) have the following meanings:

$X^3$ is F, $CF_3$ or a straight chain or branched alkyl group having from 1 to 12 carbon atoms, in which one $CH_2$-group may be replaced by —O—, —CO—O— or —O—CO—, and in which one or more hydrogen atoms may be substituted by F;

$R^1$ is hydrogen or a straight-chain or branched-chain alkyl group having from 1 to 16 carbon atoms (with or without an asymmetrical carbon atoms), in which one $CH_2$-group may be replaced by —O—, —CO—O— or —O—CO— and in which one or more hydrogen atoms may be substituted by F;

$A^1$, $A^2$ and $A^3$, independently of one another, are 1,4-phenylene in which one or two hydrogen atoms may be substituted by F, pyridine-2,5-diyl or pyrimidine-2,5-diyl, trans-1,4-cyclohexylene in which one or two hydrogen atoms may be substituted by CN, or 1,3,4-thiadiazole-2,5-diyl;

$M^1$, $M^2$, $M^3$ and $M^4$, independently of one another, are —CO—O— or —O—CO—.

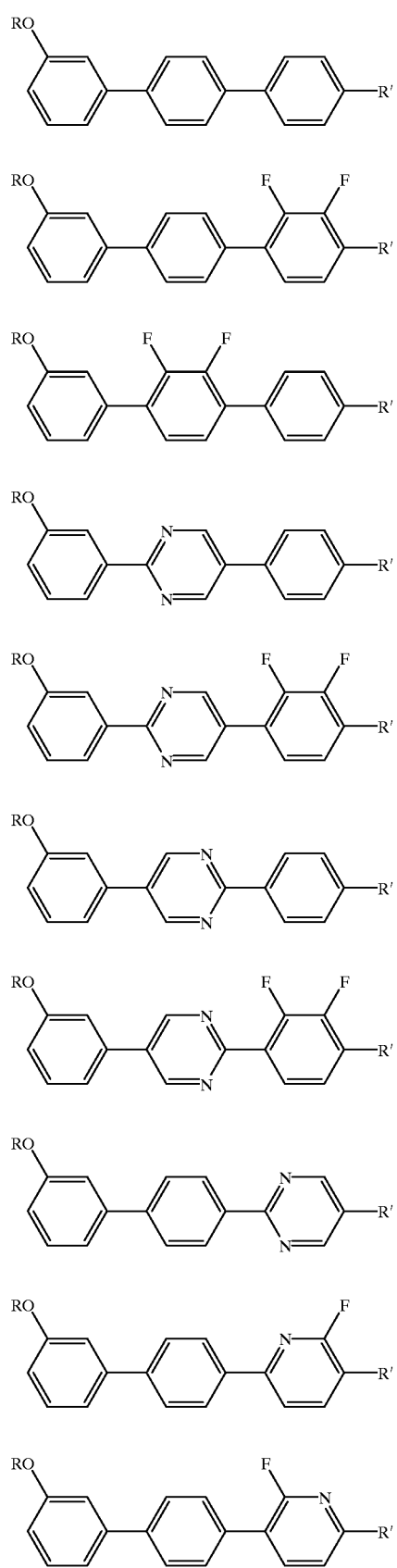
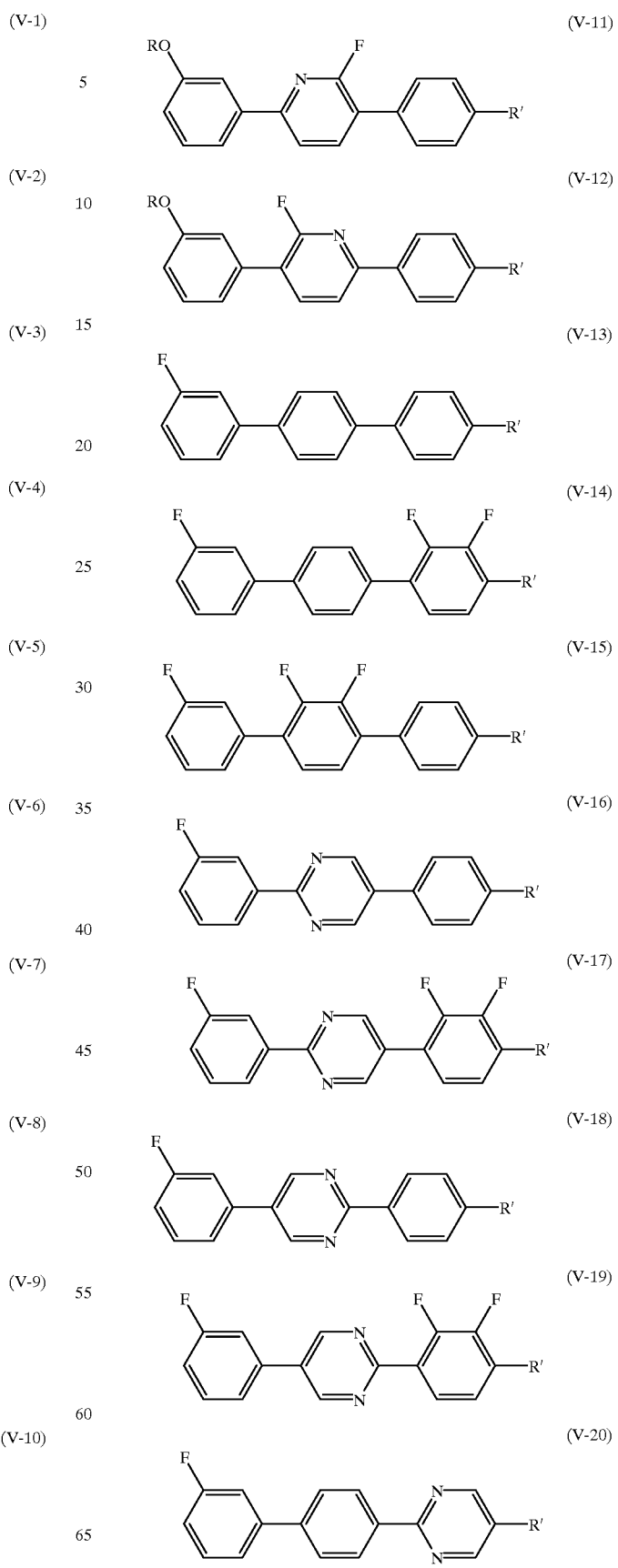

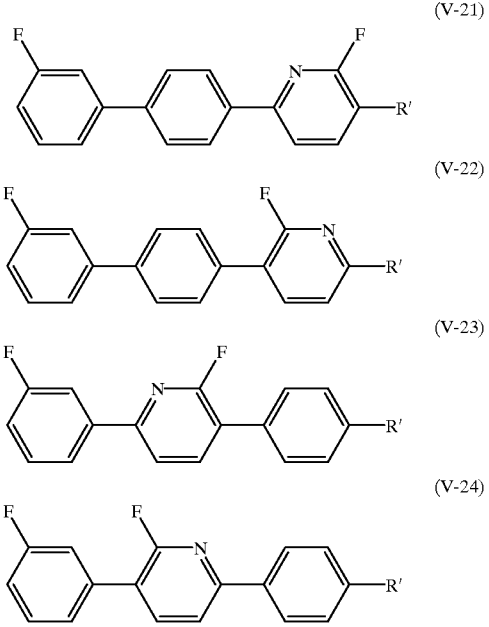

wherein R' has the same meaning as $R^1$ in formula (V).

The compounds of groups A to E are either known or can be prepared in a manner known per se, analogously to known compounds.

The compounds and synthesis thereof, are described, e.g., in:

EP-A 0 309 514 and DE-A 37 03 651 (component A);

DE-A 195 00 768 (component B);

U.S. Pat. No. 5,389,291 and WO-A 92/11 241 (component C);

EP-A 0 332 024 (component D); and

EP-A 0 578 054;

all of which are incorporated herein by reference.

The liquid crystal mixtures according to the invention are prepared in a manner which is customary per se. As a rule the components are dissolved in one another, advantageously at elevated temperatures.

Preferably the ferroelectric liquid crystal mixture according to the present invention comprises 2 to 30, more preferably 2 to 25 and in particular 2 to 20 compounds of groups A to E.

Preferably the mixture's content of compounds of groups A to E is 5% by weight or more, more preferably 10% or more, particularly 15% or more. In a preferred embodiment the mixture according to the invention comprises compounds from 2, 3 or 4 different groups A to E.

In a preferred embodiment the mixture according to the invention comprises at least one compound from group:

| a) A | b) B | c) C |
|------|------|------|
| d) D | e) E. |    |

In a further preferred embodiment the mixture according to the invention comprises 2 or more compound from at least groups:

| a) A+B | b) A+C | c) A+D |
|--------|--------|--------|
| d) A+E | e) B+C | f) B+D |
| g) B+E | h) C+D | i) C+E |
| j) D+E. |  |  |

In a further preferred embodiment the mixture according to the invention comprises 3 or more compounds from at least groups:

| a) A+B+C | b) A+B+D | c) A+B+E |
|----------|----------|----------|
| d) A+C+D | e) A+C+E | f) A+D+E |
| g) B+C+D | h) B+C+E | i) B+D+E |
| j) C+D+E. |  |  |

In a particularly preferred embodiment the mixture according to the invention includes one or more compounds of group A and one or more compounds selected from groups B to E.

In a further particularly preferred embodiment the mixture according to the invention includes one or more compounds from group B and one or more compounds from group A and C to E.

In a further particularly preferred embodiment the mixture according to the invention includes one or more compounds from group A and one or more compounds from group B.

In another particularly preferred embodiment the mixture according to the invention includes one or more compounds from group A, one or more compounds from group B and one or more compounds from groups C to E.

The liquid crystal mixtures according to the invention generally contains from 2 to 35, preferably from 2 to 30, particularly preferably from 2 to 25 compounds.

Further suitable components for the liquid crystal mixtures according to the invention include, for example:

derivatives of phenylpyrimidine, as described, for example, in WO 86/06401 and U.S. Pat. No. 4,874,542, meta-substituted aromatic compounds having a six-membered ring, as described, for example, in EP-A 0 578 054, silicon compounds, as described, for example, in EP-A 0 355 008, mesogenic compounds containing only one side chain as described, for example, in EP-A 0 541 081, hydroquinone derivatives, as described, for example, in EP-A 0 603 786, pyridylpyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, thiazoles, as described, for example, in EP-A 0 430 170, fluorinated compounds, especially terphenyles, as described, for example, in EP-A 0 132 377, 4-cyano-cyclohexyl derivatives, as described, for example, in EP-A 0 233 267, 2-fluoro-pyrazines, as described, for example in EP-A 0 532 916, naphthalene compounds, as described, for example, in DE-A 42 40 041, and thiophene compounds, as described, for example in EP-A 0 400 072.

Examples of suitable chiral, non-racemic dopes include:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, optically active tetrahydrofuran-2-carboxylic esters, as described, for example, in EP-A 0 355 561, optically active 2-fluoroalkyl ethers, as described, for example, in EP-A 0 237 007 and U.S. Pat. No. 5,051,506, and optically active 4-cyano-cyclohexyl compounds, as described, for example, in EP-A 0 428 720.

Preferred additional compounds are 4-cyano-cyclohexyls of the formula (VI):

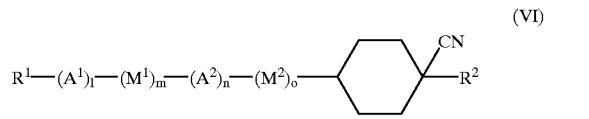

(VI)

$R^1$ and $R^2$ independently of one another, are hydrogen or a straight-chain or branched-chain alkyl group having from 2 to 16 carbon atoms (with or without an asymmetrical carbon atom), in which one or two non-adjacent —CH$_2$— groups may be replaced by —O—, —CO—, —CO—O—, —O—CO—, —CH=CH—, —C≡C— or —Si(CH$_3$)$_2$—; one or more hydrogen atoms of the alkyl group may be substituted by F, Cl, CN and/or CF$_3$; or $R^1$ is one of the following chiral groups:

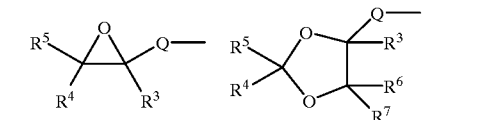

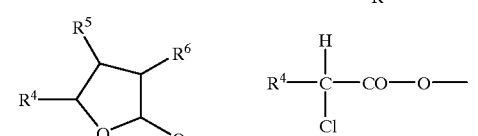

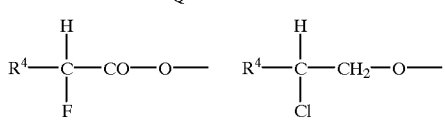

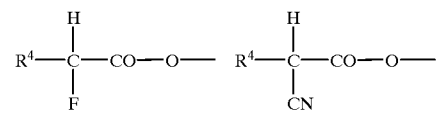

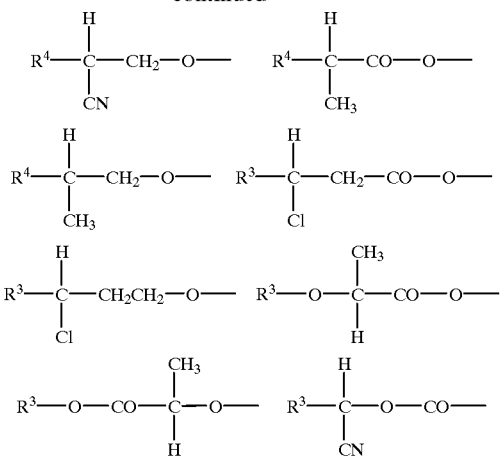

wherein $R^3$, $R^4$, $R^5$, $R^6$ and $R^7$, independently of one another, are a straight-chain or branched-chain alkyl group having from 1 to 16 carbon atoms (with or without an asymmetrical carbon atom), where one or more —CH$_2$— groups may also be replaced by —O— or —CH=CH—, with the proviso that oxygen atoms must not be bonded directly to one another; one or more hydrogen atoms of the alkyl group may be substituted by —F or —Cl; or $R^4$ and $R^5$ may also together be —(CH$_2$)$_4$— or —(CH$_2$)$_5$— if they are bonded to an oxirane, dioxolane or tetrahydrofuran system;

Q is —CH$_2$—O—, —CO—O— or a single bond;

$A^1$ and $A^2$ are identical or different and are 1,4-phenylene, in which one or two hydrogen atoms may be substituted by F, or pyrazine-2,5-diyl, pyridazine-3,6-diyl, pyridine-2,5-diyl or pyrimidine-2,5-diyl, trans-1,4-cyclohexylene in which one or two hydrogen atoms may be substituted by CN, or 1,3,4-thiadiazole-2,5-diyl, 1,3-dioxane-2,5-diyl, naphthalene-1,6-diyl;

$M^1$ and $M^2$, independently of one another, are —CO—O—, —O—CO—, —O—CO—O—, —CH$_2$—O—, —O—CH$_2$—, —CH$_2$—CH$_2$—, —CH=CH— or —CH≡C— with the proviso that $M^1$ and $M^2$ must not be bonded directly to one another;

l, m, n and o are 0 or 1, with the proviso that the sum of l+n is more than 0 and less than 4.

Examples of particulary preferred compounds of the formula (VI) include:

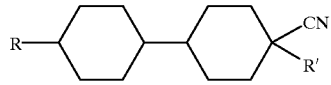

(VI-1)

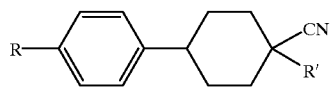

(VI-2)

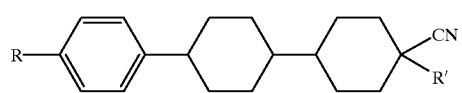

(VI-3)

-continued (VI-4)
(VI-5)
(VI-6)
(VI-7)

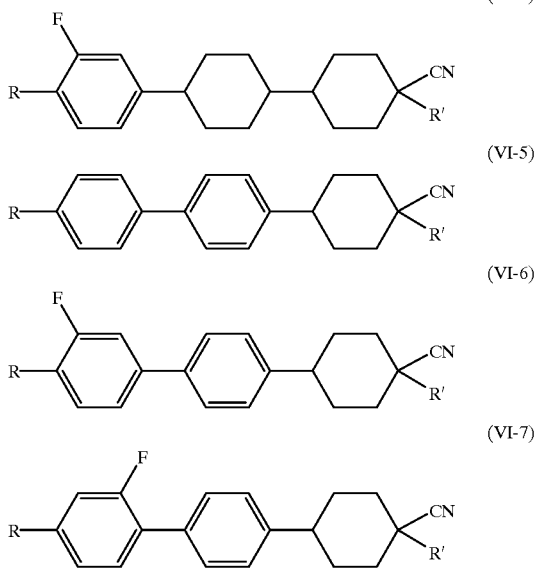

wherein R and R' have the same meanings as $R^1$ and $R^2$ in formula (VI).

Further preferred components are one or more phenylpyrimidine compounds of the formula (VII)

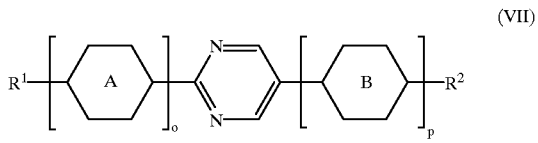

(VII)

wherein $R_1$ and $R_2$ are as defined under formula (I);

rings A and B, independently of one another, are 1,4-phenylene or a 1,4-cyclohexylene group;

o and p are 0, 1 or 2, with the proviso that $o<o+p\leq 2$; if o or p is 2 then the A or B groups can be different.

Examples of preferred compounds of the formula (VII) include:

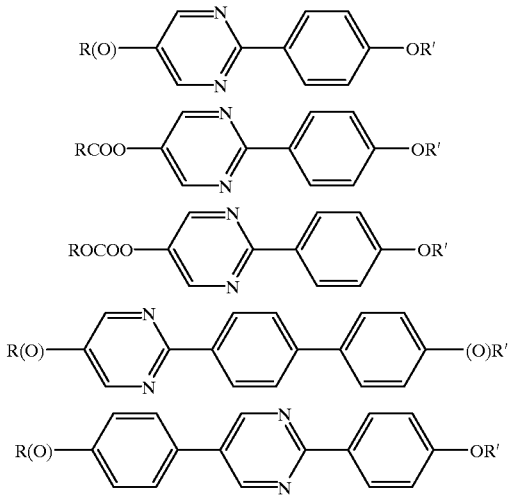

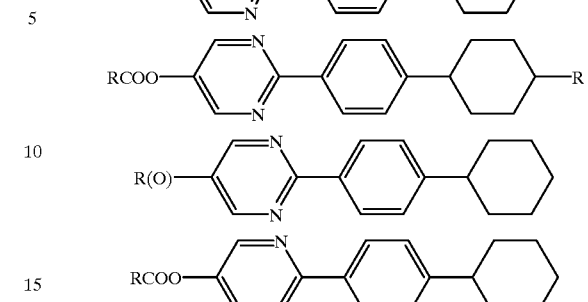

wherein R and R', independently of each other, are alkyl groups having from 1 to 12 carbon atoms.

It is preferable that the liquid crystal mixture of the present invention has a negative $\Delta\epsilon$. It is still preferable that the absolute value thereof is 2 or above, particularly 4 or above.

It is preferable that the liquid crystal mixture employed in the ferroelectric liquid crystal display device has a phase sequence of I—N*—Sa—Sc* (with decreasing temperature), a sufficiently broad N* phase and a broad Sa phase, and sufficiently long helical pitches in the N* and Sc* phases, since good alignment characteristics can be thus achieved. (I stands for the isotropic phase, N* stands for the chiral nematic phase, Sa stands for the smectic A phase, and Sc* stands for the chiral smectic C phase.) In particular, the smectic A phase should have a temperature range of 5° C. or more.

Use of the compounds of groups A to E, optionally together with the compounds of general formulae (VI) and (VII)), in accordance with the present invention allows enlargement of the absolute value of the negative $\Delta\epsilon$ of ferroelectric liquid crystals. In the conventional methods, the spontaneous polarization value of liquid crystals is selected to be sufficiently low so as to give a low driving voltage. However, the present invention makes it possible to improve the response speed by increasing the spontaneous polarization value without elevating the driving voltage. In the present invention, the spontaneous polarization value ranges preferably from 1 to 30 Nc/cm$^2$, particularly preferably from 5 to 20 Nc/cm$^2$.

With an increase in spontaneous polarization value, it is sometimes observed that sufficiently enough contrast cannot be obtained due to sticking or insufficient memory properties. It is, therefore, preferable that the ferroelectric liquid crystal mixture of the present invention has at least one compound as described, e.g., in EP-A 0 502 964, EP-A 0 385 688 or WO-A 93/04142.

Examples of these compounds include, in particular, ethylene glycol dimethyl ether and triethylene glycol dimethyl ether, and crown ethers (for example, 12-crown-4, 15-crown-5, 18-crown-6, etc.) and derivatives thereof.

It is preferable that the liquid crystal mixture of the invention contains from 0.01 to 5% by weight, particularly from 0.1 to 2% of the above compounds.

It is also preferable that the pretilt angle of liquid crystal molecules at the interface between the liquid crystal and the alignment layer is 10° or less, preferably 0.1° to 8°.

In a preferred embodiment the mixtures according to the invention show a ratio (–) (5 V)/(–) (0V) of 1.4 or more preferably 1.8 or more, particularly preferably 2.0 or more.

The mixtures according to the invention can be used in electro-optical or fully optical elements, for example display elements, switching elements, light modulators, elements for image processing and/or signal processing or generally in the area of nonlinear optics.

Liquid-crystalline mixtures according to the invention are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers 1 987).

They are expecially useful for application in the inverse or T-$V_{(min)}$ mode.

The mixtures according to the invention are characterized by an advantageous figure of merit value as defined in A. J. Staney et al., Ferroelectrics 1996, 178, 65–74 and are, therefore, especially useful for practical applications in displays.

The present invention further provides a ferroelectric liquid crystal (FLC) display device comprising the above-mentioned liquid crystal mixture of the present invention between a pair of substrates each comprising an electrode and an alignment layer formed thereon.

In a preferred embodiment the FLC display operates in the inverse mode.

Multiplexed FLC devices can operate in two different ways: the so-called "normal mode" and the so-called "inverse mode", the latter also sometimes being referred to as "T $V_{min}$-mode" or "negative dielectric mode". The distinction of both modes lies in the addressing schemes and in the different requirement with respect to the dielectric tensor of the FLC material, i.e. the FLC mixture. A survey is given, for example, in "Fast High Contrast Ferroelectric Liquid Crystal Displays and the Role of Dielectric Biaxiality" by J. C. Jones, M. J. Towler, J. R. Hughes, Displays, Volume 14, No. 2 (1993), referred to as Jones hereafter, M. Koden, Ferroelectrics 179, 121 (1996) and references cited therein.

In general, the switching characterisitcs of FLC can be discussed in terms of a diagram having the driving voltage (V) on the horizonital axis and the driving pulse width (T, time) on the vertical axis as in Jones, FIG. 8, 10 or 11.

A switching curve is determined experimentally and devides the V,T area into a switching and non-switching part. Usuall, the higher the voltage, the smaller ist the pulse width for switching. Such a behaviour is typically observed for the so-called "normal mode" FLC devices within the range of applied driving voltages.

For a suitable material, however, the V,T curve reaches a minimum (at voltage $V_{min}$) as—for example—shown in Jones, FIGS. 8, 10, 11 and then shows an upturn for higher voltages which is due to the superposition of dielectric and ferroelectric torques. FLC devices work in the inverse mode, if in the temperature range of operation, the sum of row and column driving voltage is higher than the voltage at the minimum of the V,T curve, i.e. $V_{row}+V_{col}>V_{min}$.

Several documents are cited in this application, e.g. to discuss the state of the art, synthesis of compounds used in the present invention or application of the mixtures according to the invention. All these documents are hereby incorporated by reference.

This application claims priority from Japanese patent applications 18 03 39/95 and 34 32 88/95 the content of both of which is hereby incorporated by reference.

The present invention is illustrated but not limited by the following examples.

All percentages given are by weight.

Cell Fabrication

A solution of LQT 120 (Hitachi Kasei) is applied onto glass substrates with ITO by spin coating at 2500 rpm. The substrates are heated at 200° C. for 1 hour to form a film. After rubbing the coated film with a nylon cloth in one direction, the substrates are assembled into a cell with spacers having a thickness of 2.0 μm inserted between the substrates in such a manner that the rubbing directions are parallel to each other. The properties of the liquid crystal mixture is measured using the resulting cell. The voltage (Vmin), which gives a minimum value (Tmin) of the pulse width (T) in the T–V characteristics of a ferroelectric liquid crystal device, is measured by filling the liquid crystal mixture into the cell in an isotropic phase, then applying a monopolar pulse to the cell at 25° C.

Phase transition temperatures were determined by optical polarizing microscopy and DTA.

The dielectric anisotropy (Δε) is measured by filling the liquid crystal mixture into a homotropic orientation cell and a planar orientation cell (EHC, with a cell gap of 10 μm) and applying an electric field of 1 V, 20 KHz to the cells at 25° C. The value for homotropic alignment is corrected for the tilt angle.

Spontaneous Polarization $P_s$

The Diamant bridge (or Sawver-Tower) method (H. Diamant, K. Prenck and R. Pepinsky, Rev. Sci. Instr. 28, 30 (1957)) is used to determine $P_s$. The test cells have a thickness of 5 μm and are thinly coated with ITO.

2 (−) (5 V) was measured by optical inspection of two memory states under applying a high frequency rectangular pulse. The voltage of the rectangular pulse from peak to peak is 10 V.

EXAMPLE 1

FELIX-M4851/000 and FELIX-M4851/100 (Hoechst AG) are mixed with the compounds shown below in accordance with the present invention in the indicated ratio (wt %) to prepare a liquid crystal mixture A.

The phase transition temperatures, the spontaneous polarization (Ps), the dielectric anisotropy (Δε), the voltage at a minimum pulse width (Vmin), the minimum pulse width (Tmin), and the effective cone angle under applying a high-frequency rectangular pulse (2 θ) of the liquid crystal mixture A are shown below.

|  | ratio |
|---|---|
| FELIX-M4851/000 | 51 |
| FELIX-M4851/100 | 29 |
| Compound a | 10 |
| Compound b | 10 |

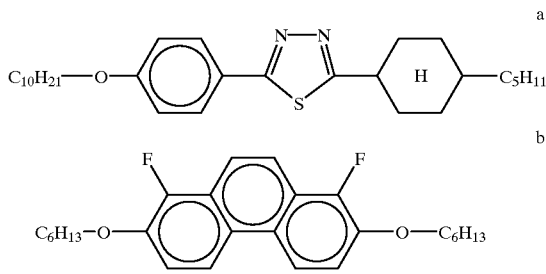

Liquid Crystal Mixture A:
  Phase transition temperature:
    Sc 64.3 Sa 77.2 N 81.4 I
  Ps: −8.2 nC/cm$^2$
  Δε: −2.7
  τmin: 12 μs
  Vmin: 23 V/μm
  2 θ5V: 27.4°

COMPARATIVE EXAMPLE 1

FELIX-M4851/000 and FELIX-M4851/100 (Hoechst AG) are mixed with the compounds shown below in the indicated ratio (wt %) to prepare liquid crystal mixtures B and C, in which the concentration of the chiral dopants is almost the same as that of the liquid crystal mixture A described in Example 1. The phase transition temperature, the spontaneous polarization (Ps), the dielectric anisotropy (Δε), the voltage at a minimum pulse width (Vmin), the minimum pulse width (τmin), and the effective cone angle under applying a high-frequency rectangular pulse (2 θ) of the liquid crystal mixtures B and C are shown below.

|  | ratio | |
| --- | --- | --- |
|  | B | C |
| FELIX-M4851/000 | 76 | 64 |
| FELIX-M4851/100 | 24 | 26 |
| Compound b |  | 10 |

Liquid Crystal Mixture B:
  Phase transition temperature:
    Sc 62.7 Sa 68.7 N 72.7–74.4 I
  Ps: 8.5 nC/cm$^2$
  Δε: −0.8
  τmin: 7 μs
  Vmin: 65 V/μm
  2 θ (5 V): 17.3°
Liquid Crystal Mixture C:
  Phase transition temperature:
    Sc 55.5 Sa 68.7 N 72.9–75.0 I
  Ps: 7.5 nC/cm$^2$
  Δε: −1.1
  τmin: 9 μs
  Vmin: 45 V/μm
  2 θ (5 V): 23°

The liquid crystal mixture A described in Example 1 has a value of Vmin lower than that of the liquid crystal mixtures B and C, and it can be driven under a low voltage. It also has a lower value of Δε.

EXAMPLE 2

FELIX-M4851/000 and FELIX-M4851/100 (Hoechst AG) are mixed with the groups of the compounds (d, e and f) in accordance with the present invention in the indicated ratio (wt %) to prepare liquid crystal mixtures D, E and F.

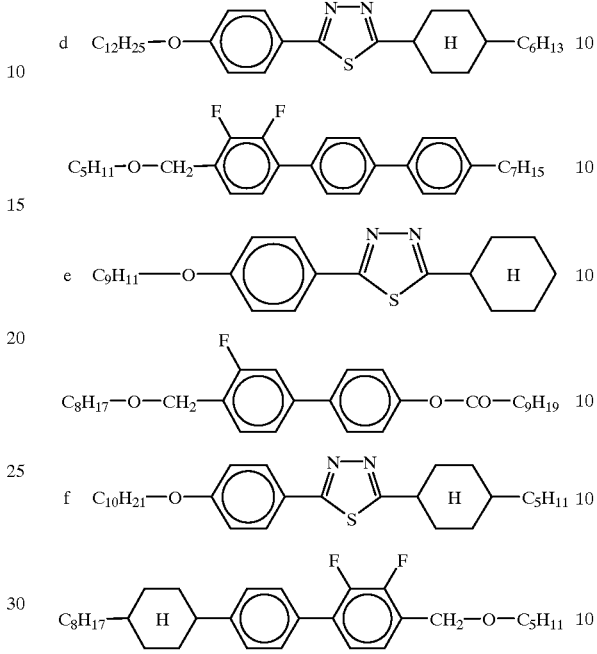

The phase transition temperature, the spontaneous polarization (Ps), the effective cone angle under applying a high-frequency rectangular pulse (2 θ), the voltage at a minimum pulse width (Vmin) and the minimum pulse width (τmin) of each of the liquid crystal mixtures are shown below.

TABLE 2

| Phase transition temperature: | Sc | Sa | N | I |
| --- | --- | --- | --- | --- |
| D | 62.8 | 71.8 | 75.3–77.0 | |
| E | 62.2 | 66.0 | 69.5–71.2 | |
| F | 59.2 | 73.9 | 77.2–80.0 | |

|  | Ps (nC/cm$^2$) | τmin (μs) | Vmin (V/μm) | 2θ (5V) (°) |
| --- | --- | --- | --- | --- |
| D | −8.6 | 9.2 | 35 | 20.2 |
| E | −8.6 | 10.0 | 45 | 24.8 |
| F | −8.4 | 8.8 | 30 | 19.8 |

EXAMPLE 3

FELIX-M4851/000 and FELIX-M4851/100 (Hoechst AG) are mixed with the compounds (g) shown below in the indicated ratio (wt %) to prepare a liquid crystal mixture G, in which the concentration of the chiral dopants is almost the same as that of the liquid crystal mixture A described in Example 1. The phase transition temperature, the spontaneous polarization (Ps), the effective cone angle under applying a high-frequency rectangular pulse (2 θ), the voltage at a minimum pulse width (Vmin) and the minimum pulse width (τmin) of the liquid crystal mixture G are shown below.

| | ratio |
|---|---|
| FELIX-M4851/000 | 39 |
| FELIX-M4851/100 | 31 |
| Compound Group g | 10 each |

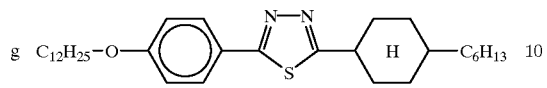

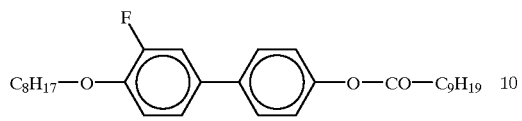

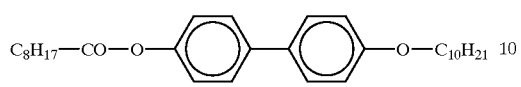

Liquid Crystal Mixture G:

Phase transition temperature:
Sc 62.9 Sa 67.1 N 70.3–71.8 I

Ps: −8.7 nC/cm²

τmin: 16.0 μs

Vmin: 35 V/μm

2 θ (5 V): 24.6°

EXAMPLE 4

The compounds shown below are mixed in the indicated ratio (wt %) to prepare a liquid crystal mixture H.

The phase transition temperature, the spontaneous polarization (Ps), the dielectric anisotropy (Δε), the voltage at a minimum pulse width (Vmin) and the minimum pulse width (τmin) of the liquid crystal mixture H are shown below.

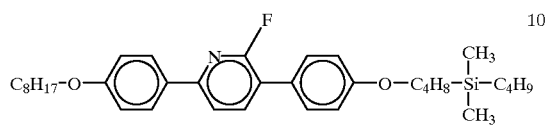

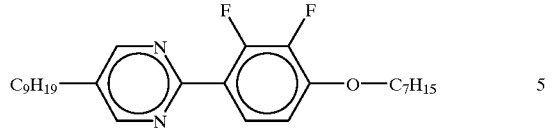

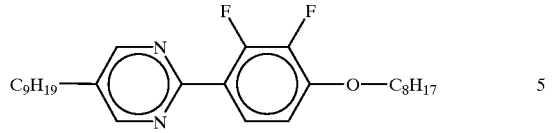

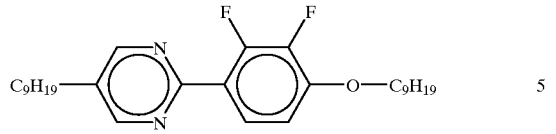

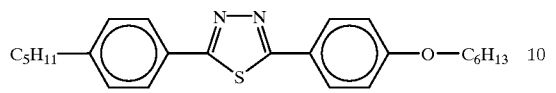

Liquid Crystal Mixture H:

Phase transition temperature:
Sc 71.8 Sa 73.3 N 87.0–89.7 I

Ps: 8.0 nC/cm²

Δε: −4.0

τmin: 13 μs

Vmin: 33 V/μm

EXAMPLE 5

FELIX-M4851/000 and FELIX-M4851/100 (Hoechst AG) are mixed with the compounds shown below in accordance with the present invention in the indicated ratio (wt %) to prepare a liquid crystal mixture J.

The phase transition temperature, the spontaneous polarization (Ps), the dielectric anisotropy (Δε), the voltage at a minimum pulse width (Vmin) and the minimum pulse width (τmin) of the liquid crystal mixture J are shown below.

|  | ratio |
| --- | --- |
| FELIX-M4851/000 | 65 |
| FELIX-M4851/100 | 15 |
| Compounds J (2 compounds as follows) | 10 each |

C$_9$H$_{19}$—O—[phenyl]—[thiadiazole]—[cyclohexyl]—H

C$_3$H$_7$—O—[phenyl]—[pyrimidine]—[phenyl]—O—C$_8$H$_{17}$

Liquid Crystal Mixture J:
  Phase transition temperature:
    Sc 60.0 Sa 66.3 N 68.3–70.1 I
  Ps: −3.8 nC/cm$^2$
  Δε: −2.5
  τmin: 25 μs
  Vmin: 20 V/μm

COMPARATIVE EXAMPLE 2

The phase transition temperature, the spontaneous polarization (Ps), the dielectric anisotropy (Δε), the voltage at a minimum pulse width (Vmin) and the minimum pulse width (τmin) of FELIX-M4851/000, which has a similar concentration of the chiral dopants as that of the liquid crystal mixture J, are shown below.

Phase transition temperature:
    Sc 64 Sa 70 N 74 I
  Ps: −4.0 nC/cm$^2$
  Δε: −0.5
  τmin: 17 μs
  Vmin: 40 V/μm In the liquid crystal mixture J described in Example 5, the value of Vmin is lower than that of FELIX-M4851/000, and thus it can be driven under a low voltage. It also has a lower value of Δε.

EXAMPLE 6

A liquid crystal mixture K contains the following components

C$_8$H$_{17}$—[pyridine]—[phenyl]—O—C$_8$H$_{17}$  19%

C$_8$H$_{17}$—O—[pyrimidine]—[phenyl]—O—C$_8$H$_{17}$  7%

C$_8$H$_{17}$—[pyridine]—[phenyl]—O—C$_{10}$H$_{21}$  15%

C$_8$H$_{17}$—O—[pyrimidine]—[phenyl]—O—C$_6$H$_{13}$  13%

C$_8$H$_{17}$—O—[pyrimidine]—[phenyl]—O—C$_4$H$_9$  13%

C$_8$H$_{17}$—O—[pyrimidine]—[phenyl]—O—C$_{10}$H$_{21}$  13%

C$_8$H$_{17}$—O—[pyrimidine]—[phenyl]—O—C$_6$H$_{13}$  20%

The following compounds are added to the liquid crystal mixture K to prepare a liquid crystal mixture L.

C$_6$H$_{13}$—[pyridine]—[thiadiazole]—[phenyl]—O—C$_9$H$_{19}$  10%

C$_4$H$_9$—Si(CH$_3$)$_2$—C$_4$H$_8$—O—[difluorophenyl]—[phenyl]—[cyclohexyl]—C$_5$H$_{11}$  10%

C$_8$H$_{17}$—O—[difluorophenyl]—[phenyl]—O—CO—C*(R)—C*(R)(epoxide)—C$_3$H$_7$  1%

C$_6$H$_{13}$—O—[naphthyridine/fluoronaphthalene]—O—C$_6$H$_{13}$  10%

The phase transition temperature, the spontaneous polarization (Ps), the voltage at a minimum pulse width (Vmin) and the minimum pulse width (τmin) of the liquid crystal mixture E are shown in Table 1.

Table 1
  Phase transition temperature:
    X −5 Sc* 62.5 Sa 79.4 N* 83.3–85.0 I
  Ps: 3.3 nC/cm2
  Δε: −1.5
  τmin: 20 μs
  Vmin: 33 V

EXAMPLE 7

The following compounds are added to the liquid crystal mixture K to prepare a liquid crystal mixture M.

C$_8$H$_{17}$—O—[difluorophenyl]—[phenyl]—O—CO—C*(R)—C*(R)(epoxide)—C$_3$H$_7$  1%

-continued

[C9H19-pyrimidine-(2,3-difluorophenyl)-O-C7H15] 9%

[C9H19-pyrimidine-(2,3-difluorophenyl)-O-C8H15] 9%

[C9H19-pyrimidine-(2,3-difluorophenyl)-O-C9H19] 9%

The phase transition temperature, the spontaneous polarization (Ps), the voltage at a minimum pulse width (Vmin) and the minimum pulse width (τmin) of the liquid crystal mixture M are shown in Table 2.

Table 2

Phase transition temperature:
  X 6 Sc* 65.5 Sa 69.4 N* 74.5–75.0 I
Ps: 3.3 nC/cm2
Δε: −1.2
τmin: 24 μs
Vmin: 51 V

EXAMPLE 8

A liquid crystal mixture N was prepared containing the following components:

[C8H17-pyrimidine-phenyl-O-C8H17] 19.42%

[C8H17-pyrimidine-phenyl-O-C10H21] 15.44%

[C8H17-O-pyrimidine-phenyl-O-C4H9] 12.82%

[C8H17-pyrimidine-phenyl-O-C6H13] 20.10%

-continued

[C8H17-O-pyrimidine-phenyl-O-C8H17] 6.5%

[C8H17-O-pyrimidine-phenyl-O-C6H13] 13.11%

[C8H17-O-pyrimidine-phenyl-O-C10H21] 12.61%

EXAMPLES 9 to 12

Four liquid crystal mixtures were prepared, consisting the following compounds:

Mixture N: 58%

[C8H17O-pyrimidine-phenyl-OC2H5] 10%

[C9H19-O-pyrimidine-thiadiazole-cyclohexyl-H] 10%

[C4H9-Si(CH3)2-C4H9-O-(fluoropyridine)-phenyl-cyclohexyl-H-C5H11] 10%

[C7H15-CN-cyclohexyl-H-phenyl-phenyl-OCH2-CHF-C6H13] 3% and 10%, respectively, one of the following compounds shown in the table.

The phase transition temperature ($T_{C/A}$, T), the spontaneous polarization (Ps), the voltage at a minimum pulse width ($V_{min}$), the minimum pulsewidth (τmin), and the effective cone angle under applying a high frequency rectangular pulse ($V_{pk-pk}$=10 V:2 θ (5 V), $V_{pk-pk}$=20 V:2 θ (10 V)) of mixtures are shown in the table.

| Examples 9 to 12 | |
|---|---|
| Ex. | Structure |
| 9 | 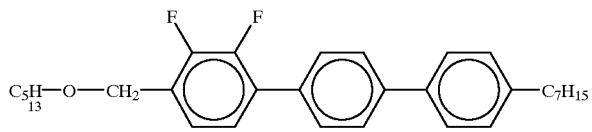 |
| 10 | 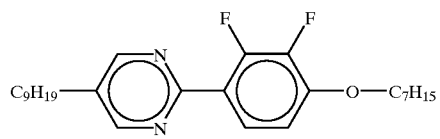 |
| 11 | 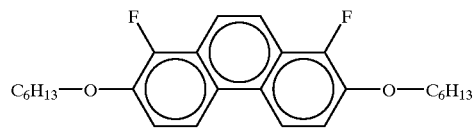 |
| 12 | 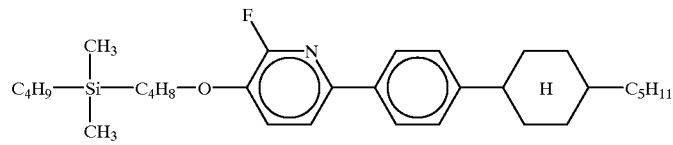 |

| | | | | phases and EO properties | | | | |
|---|---|---|---|---|---|---|---|---|
| Ex. | M.P. [°] | $T_{C/A}$ [°] | $T_{A/N}$ [°] | $T_{N/I}$ [°] | Ps vis. [nC/cm$^2$] | Vmin [V] | tmin [µs] | 2θ(5 V) [°] | 2θ(10 V) [°] |
| 9 |  | 64 | 75 | 79 | 3.2 | 45 | 17 | 22 | 33 |
| 10 | −10 | 66 | 74 | 79 | 4.3 | 41 | 34 | 19 | 30 |
| 11 | −10 | 58 | 78 | 83 | 3.1 | 29 | 50 | 15 | 24 |
| 12 | −10.9 | 70 | 79 | 64 |  | 42 | 68 | 20 | 31 |

EXAMPLES 13 to 31

The following liquid crystal mixtures were prepared:
Mixture N: 68%

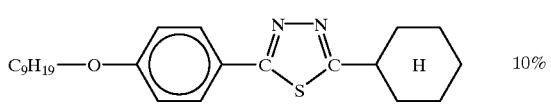 10%

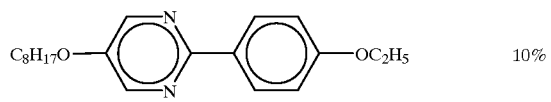 10%

-continued

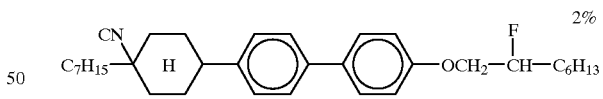 2% and 10%, respectively, one of the following compounds shown in the table. The phase transition temperature ($T_{C/A}$, T), the spontaneous polarization (Ps), the voltage at a minimum pulse width ($V_{min}$), the minimum pulsewidth (Tmin), and the effective cone angle under applying a high frequency rectangular pulse ($V_{pk-pk}$=10 V:2 θ (5 V), $V_{pk-pk}$= 20 V:2 θ (10 V)) of mixtures are shown in the table.

Examples 13 to 31

| Ex. | Structure | M.P. [°] | $T_{C/A}$ [°] | $T_{A/N}$ [°] | $T_{N/I}$ [°] | Ps vis. [nC/cm²] | Vmin [V] | tmin [μs] | 2θ(5 V) [°] | 2θ(10 V) [°] |
|---|---|---|---|---|---|---|---|---|---|---|
| 13 | C₈H₁₇O—[pyrazine]—[phenyl]—CO—O—[phenyl(F,F)]—O—C₈F₁₇ | −5.42 | 67 | 79 | 87 | 4.7 | 46 | 28 | 17 | 26 |
| 14 | C₆H₁₃O—[pyridine(F)]—[phenyl]—[cyclohexyl]—C₅H₁₁ | −0.23 | 70 | 77 | 87 | 3.9 | 54 | 31 | 11 | 26 |
| 15 | C₁₀H₂₁O—[pyridine(F)]—[phenyl]—[cyclohexyl]—C₅H₁₁ | −8.32 | 68 | 75 | 84 | 3.5 | 67 | 20 | 17 | 26 |
| 16 | C₁₀H₂₁—[pyridine(F,F)]—[phenyl]—O—C₈H₁₇ | −4.22 | 64 | 73 | 79 | 3.0 | 53 | 20 | 16 | 25 |
| 17 | C₈H₁₇—[pyridine(F,F)]—[phenyl]—O—C₆H₁₃ | −1.82 | 62 | 70 | 77 | 3.7 | 51 | 23 | 16 | 26 |

-continued
Examples 13 to 31
| Ex. | Structure | M.P. [°] | T_C/A [°] | T_A/N [°] | T_N/I [°] | Ps vis. [nC/cm²] | Vmin [V] | tmin [µs] | 2Θ(5 V) [°] | 2Θ(10 V) [°] |
|---|---|---|---|---|---|---|---|---|---|---|
| 18 | 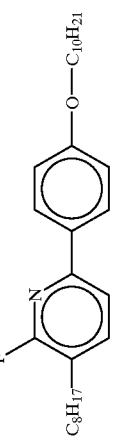 | 11.03 | 66 | 75 | 80 | 3.6 | 55 | 22 | 17 | 26 |
| 19 | 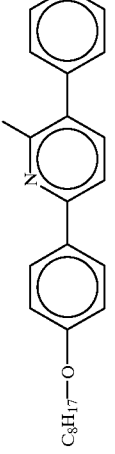 | −6.32 | 71 | 78 | 87 | 4.0 | 55 | 18 | 13 | 23 |
| 20 | 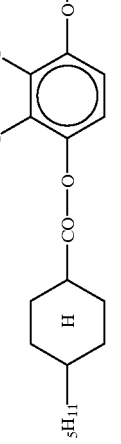 |  | 56 | 65 | 79 | 3.4 | 53 | 24 | 13 | 22 |
| 21 | 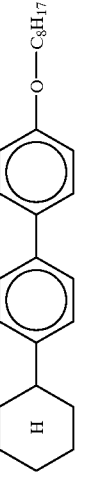 | −0.58 | 54 | 63 | 76 | 2.9 | 55 | 23 | 14 | 24 |
| 22 | 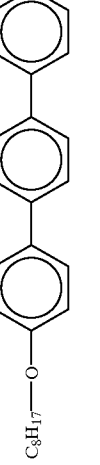 | −4.22 | 58 | 72 | 83 |  | 62 | 18 | 11 | 18 |

-continued

Examples 13 to 31

| Ex. | Structure | M.P. [°] | T$_{C/A}$ [°] | T$_{A/N}$ [°] | T$_{N/I}$ [°] | Ps vis. [nC/cm²] | Vmin [V] | tmin [µs] | 2θ(5 V) [°] | 2θ(10 V) [°] |
|---|---|---|---|---|---|---|---|---|---|---|
| 23 | C$_8$H$_{17}$—O—[ring]F,F—[ring]—[ring]—CH$_2$—O—C$_5$H$_{11}$ | 19.43 | 65 | 76 | 82 | 3.5 | 50 | 32 | 17 | 23 |
| 24 | CH$_3$—O—CH$_2$—[ring]F,F—[ring]—[ring]—O—C$_8$H$_{17}$ | −4.95 | 65 | 78 | 85 | 0 | 57 | 21 | 16 | 23 |
| 25 | C$_5$H$_{11}$—O—CH$_2$—[ring]F,F—[ring]—[ring]—C$_7$H$_{15}$ | −6.32 | 61 | 75 | 80 | 1.1 | 68 | 18 | 16 | 23 |
| 26 | C$_8$H$_{17}$—O—[quinoline-N,N]—O—C$_6$H$_{13}$ | | 53 | 74 | 78 | | 67 | 20 | 11 | 16 |
| 27 | C$_6$H$_{13}$—O—[ring-F]—[ring]—[ring-F]—O—C$_6$H$_{13}$ | −4.95 | 53 | 76 | 82 | 2.8 | 36 | 30 | 15 | 24 |

-continued

Examples 13 to 31

| Ex. | Structure | M.P. [°] | T_C/A [°] | T_A/N [°] | T_N/I [°] | Ps vis. [nC/cm²] | Vmin [V] | tmin [µs] | 2φ(5 V) [°] | 2φ(10 V) [°] |
|---|---|---|---|---|---|---|---|---|---|---|
| 28 | C₉H₁₉–(pyridine)–(difluorophenyl)–O–C₇H₁₅ | −4.22 | 63 | 72 | 78 | 4.1 | 48 | 22 | 17 | 26 |
| 29 | C₉H₁₉–(pyridine)–(difluorophenyl)–O–C₈H₁₇ | −5.27 | 64 | 73 | 80 | 3.4 | 49 | 22 | 16 | 26 |
| 30 | C₉H₁₉–(pyridine)–(difluorophenyl)–O–CO–(cyclohexyl)–C₅H₁₁ | | 65 | 67 | 86 | 3.8 | 56 | 25 | 13 | 21 |
| 31 | C₉H₁₉–(pyridine)–(difluorophenyl)–O–CO–(cyclohexyl)–C₅H₁₁ | | 67 | 71 | 84 | 3.7 | 50 | 25 | 15 | 24 |

We claim:
1. A ferroelectric liquid crystal mixture comprising at least two compounds selected from at least two different of the following groups of compounds including two more compounds from at least groups B and C:

A. (1,3,4)-Thiadiazole derivatives of the formula (I):

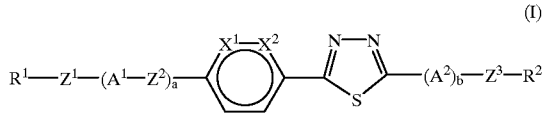

(I)

wherein the symbols and indices have the following meanings:
$R^1$ and $R^2$ independently of one another, are
(a) a hydrogen atom,
(b) a straight-chain or branched-chain alkyl group, with or without an asymmetric carbon atom, having from 2 to 16 carbon atoms, in which one or two —$CH_2$— groups may be replaced by —O—, —S—, —CO—, —CO—O—, —O—CO—, —CH=CH—, —C≡C—, —Si(CH$_3$)$_2$—, 1,4-cyclohexylene, 1,4-phenylene, cyclopropane-1,2-diyl or —O—CO—O—, with the proviso that —O— and/or —S— atoms must not be directly bonded to one another; one or more hydrogen atoms of the alkyl group may be substituted by F, Cl, CN and/or CF$_3$; or
(c) any one of the following chiral groups:

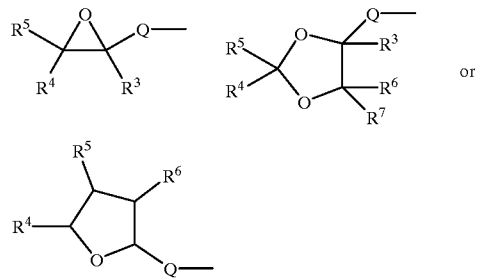

wherein $R^3$, $R^4$, $R^5$, $R^6$ and $R^7$, independently of one another, are a straight-chain or branched-chain alkyl group having from 1 to 16 carbon atoms (with or without an asymmetrical carbon atom), where one or more —$CH_2$— groups may also be replaced by —O— or —CH=CH—, with the proviso that oxygen atoms must not be bonded directly to one another; one or more hydrogen atoms of the alkyl group may be substituted by —F or —Cl; or $R^4$ and $R^5$ may also together be —(CH$_2$)$_4$— or —(CH$_2$)$_5$— if they are bonded to an oxirane, dioxolane or tetrahydrofuran system;

Q is —$CH_2$—O—, —CO—O— or a single bond;

$Z^1$, $Z^2$ and $Z^3$ independently of one another, are a single bond, —O—, —CO—O— or —O—CO—; with the proviso that, when $R^1$ is (c), then $Z^1$ is not a single bond, and that, when $R^2$ is (c), then $Z^2$ is not a single bond;

$A^1$ and $A^2$ are identical or different and are 1,4-phenylene, in which one or more H atoms may be replaced by F, pyridine-2,5-diyl, in which one H atom may be replaced by F, pyrimidine-2,5-diyl or trans-1,4-cyclohexylene;

a and b are 0 or 1 and a+b is 0 or 1;

$X^1$ and $X^2$ independently of one another, are —N—, —CF— or —CH—;

B. Phenanthrene derivatives of the formula (II),

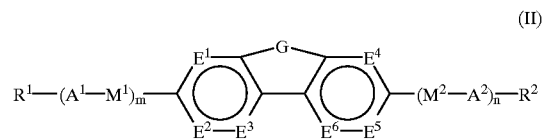

(II)

in which the symbols and indices have the following meanings:
$E^1$, $E^2$, $E^3$, $E^4$, $E^5$ and $E^6$ are —N—, —CF— or —CH—, with the following provisos:
if $E^1$ ($E^4$) is —N— or —CF—, $E^2$ and $E^3$ ($E^5$ and $E^6$) must be —CH—;
if $E^2$ and/or $E^3$ ($E^5$ and/or $E^6$) are —CF—, $E^1$ ($E^4$) must be —CH—;
if $E^2$ ($E^5$) is —N—, $E^1$ ($E^4$) must be —CH—, while $E^3$ ($E^6$) can be —CH— or —CF—; and
at least one of $E^1$ to $E^6$ must be —N— or —CF—;

G is —$CH_2CH_2$— or —CH=CH—;

$R^1$ and $R^2$, independently of one another, are hydrogen or a straight-chain or branched-chain alkyl group having from 1 to 20 carbon atoms (with or without an asymmetrical carbon atom), in which one or more —$CH_2$— groups may be replaced by —O—, —CO—O—, —O—CO—, —O—CO—O—, —CH=CH—, —C≡C—, cyclopropane-1,2-diyl, —Si(CH$_3$)$_2$—, 1,4-phenylene, trans-1,4-cyclohexylene or trans-1,3-cyclopentylene, with the proviso that oxygen atoms and/or sulfur atoms must not be bonded directly to one another; one or more hydrogen atoms of the alkyl group may be substituted by —F, —Cl, —Br, —CF$_3$, —CN or —OR$^3$; or $R^1$, $R^2$ are one of the following chiral groups:

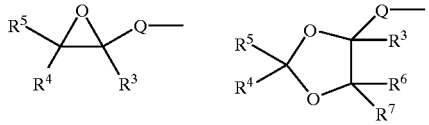

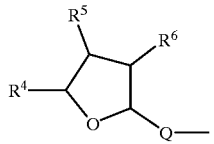

wherein $R^3$, $R^4$, $R^5$, $R^6$ and $R^7$, independently of one another, are a straight-chain or branched-chain alkyl group having from 1 to 6 carbon atoms (with or without an asymmetrical carbon atom), where one or more —$CH_2$— groups may also be substituted by —O— or —CH=CH—, with the proviso that oxygen atoms must not be bonded directly to one another; one or more hydrogen atoms of the alkyl group may be substituted by —F or —Cl; or $R^4$ and $R^5$ may also together be —(CH$_2$)$_4$— or —(CH$_2$)$_5$— if they are bonded to an oxirane, dioxolane or tetrahydrofuran system;

Q is —$CH_2$—O—, —CO—O— or a single bond;

$M^1$ and $M^2$, independently of one another, are —CO—O—, —O—CO—, —$CH_2$—O—, —O—$CH_2$—, —$CH_2$—$CH_2$—, —C≡C— or a single bond;

$A^1$ and $A^2$, independently of one another, are 1,4-phenylene in which one or more hydrogen atoms may be substituted by F, Cl and/or CN, pyrazine-2,5-diyl pyridazine-3,6-diyl, pyridine-2,5-diyl in which one or more hydrogen atoms may be substituted by F, pyrimidine-2,5-diyl, trans-1,4-cyclohexylene in which one or two hydrogen atoms may be substituted with CN and/or $CH_3$;

n and m are 0 or 1, and the sum of n+m is 0 or 1;

C. 2-Fluoropyridine derivatives of the formula (III),

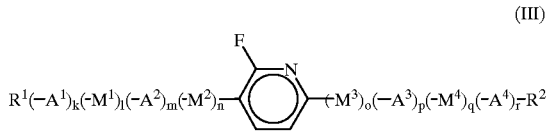
(III)

in which the symbols and indices have the following meanings:

$R^1$ and $R^2$, independently of one another, are hydrogen or a straight-chain or branched-chain alkyl group having from 1 to 16 carbon atoms (with or without an asymmetrical carbon atom), in which one or two non-adjacent —$CH_2$— groups may be replaced by —O—, —CO—, —CO—O—, —O—CO—, —O—CO—O—, —CH=CH—, —C≡C—, cyclopropane-1,2-diyl or —$Si(CH_3)_2$—; one or more hydrogen atoms of the alkyl group may be substituted by F, Cl, CN and/or $CF_3$; or $R^1$, $R^2$ are one of the following chiral groups:

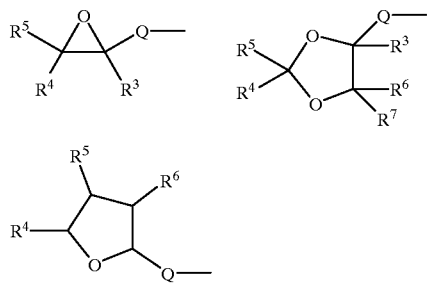

wherein $R^3$, $R^4$, $R^5$, $R^6$ and $R^7$, independently of one another, are a straight-chain or branched-chain alkyl group having from 1 to 16 carbon atoms (with or without an asymmetrical carbon atom), where one or more —$CH_2$— groups may also be substituted by —O— or —CH=CH—, with the proviso that oxygen atoms must not be bonded directly to one another; one or more hydrogen atoms of the alkyl group may be substituted by —F or —Cl; or $R^4$ and $R^5$ may also together be —$(CH_2)_4$— or —$(CH_2)_5$— if they are bonded to an oxirane, dioxolane or tetrahydrofuran system;

Q is —$CH_2$—O—, —CO—O— or a single bond;

$A^1$, $A^2$, $A^3$ and $A^4$, independently of one another, are 1,4-phenylene in which one or two hydrogen atoms may be substituted by F, or pyrazine-2,5-diyl, pyridazine-3,6-diyl, pyridine-2,5-diyl or pyrimidine-2, 5-diyl, trans-1,4-cyclohexylene in which one or two hydrogen atoms may be substituted by CN, or naphthalene-2,6-diyl; $M^1$, $M^2$, $M^3$ and $M^4$, independently of one another, are —O—, —S—, —CO—, —CO—O—, —O—CO—, —O—CO—O—, —$CH_2$—O—, —O—$CH_2$—, —$CH_2$—$CH_2$—, —CH=CH— or —C≡C— with the proviso that two M groups must not be directly bonded to one another; k, l, m, n, o, p, q and r are 0 or 1, with the proviso that the sum of k+m+p+r is more than 0 and less than 4;

D. Phenylene derivatives of the formula (IV),

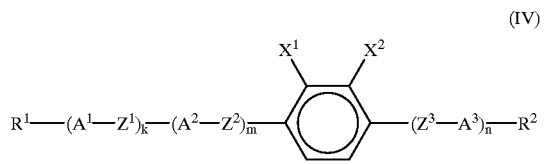
(IV)

wherein $R^1$ and $R^2$, independently of one another, are hydrogen or a straight-chain or branched-chain alkyl group having from 1 to 16 carbon atoms (with or without an asymmetrical carbon atom), in which one or two non-adjacent —$CH_2$— groups may be replaced by —O—, —CO—, —CO—O—, —O—CO—, —O—CO—O—, —CH=CH—, —C≡C—, cyclopropane-1,2-diyl, 1,4-phenylene, 1,4-Cyclohexylene or —$Si(CH_3)_2$—; and one or more hydrogen atoms of the alkyl group may be substituted with F, Cl, CN and/or $CF_3$; or $R^1$, $R^2$ are one of the following chiral groups:

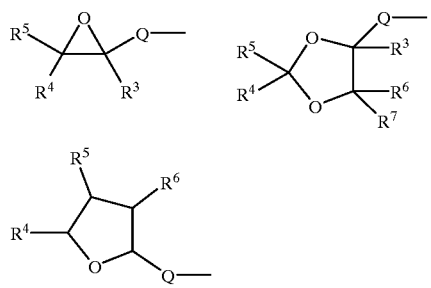

wherein $R^3$, $R^4$, $R^5$, $R^6$ and $R^7$, independently of one another, are a straight-chain or branched-chain alkyl group having from 1 to 16 carbon atoms (with or without an asymmetrical carbon atom), where one or more —$CH_2$— groups may also be substituted by —O— or —CH=CH—, with the proviso that oxygen atoms must not be bonded directly to one another; one or more hydrogen atoms of the alkyl group may be substituted by —F or —Cl; or $R^4$ and $R^5$ may also together be —$(CH_2)_4$— or —$(CH_2)_5$— if they are bonded to an oxirane, dioxolane, or tetrahydrofuran system;

Q is —$CH_2$—O—, —CO—O— or a single bond;

$A^1$, $A^2$, $A^3$ are, independently of one another, 1,4-phenylene in which one two H-atoms may be substituted by F, pyridin-2,5-diyl, pyrimidin-2,5-diyl, pyrazine-2,5-diyl, pyridazin-3,6-diyl, naphthalene-2,6-diyl, 1,2,3,4-tetrahydronapthalene-2,6-diyl or 1,4-cyclohexylene in which one or two hydrogenatoms may be substituted by CN and/or $CH_3$ groups;

$X^1$ and $X^2$ are selected from hydrogen, F, Cl, $CF_3$ and CN; with the proviso that $X^1$ and $X^2$ are not simultaneously hydrogen;

each of $Z^1$ and $Z^2$ are —CO—O—, —O—CO—, —$CH_2CH_2$—, —O—$CH_2$—, —$CH_2$—O—, —C≡C— or a single bond;

each k, m and n are 0, 1 or 2, and (k,m+n) is 1 or 2; and

E. Meta-substituted aromatic compounds of the formula (V),

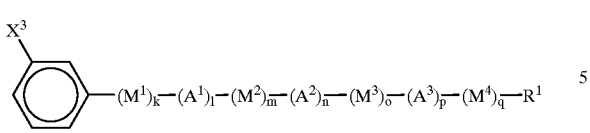

wherein $X^3$ is F, Cl, Br, CN, $CF_3$ or an alkyl group having from 1 to 12 carbon atoms, in which one or two $CH_2$-group may be replaced by —O—, —CO—O— or —O—CO—, and in which one or more hydrogen atoms in the alkyl group may be substituted by F, Cl or CN;

$R^1$ is hydrogen or a straight-chain or branched-chain alkyl group having from 1 to 16 carbon atoms (with or without an asymmetrical carbon atom), in which one or more hydrogen atoms may be substituted by F, Cl, CN and/or $CF_3$;

$A^1$, $A^2$ and $A^3$, independently of one another, are 1,4-phenylene in which one or two hydrogen atoms may be substituted by F, or pyrazine-2,5-diyl, pyridazine-3,6-diyl, pyridine-2,5-diyl or pyrimidine-2,5-diyl, trans-1,4-cyclohexylene in which one or two hydrogen atoms may be substituted by CN, or 1,3,4-thiadiazole-2,5-diyl, 1,3-dioxane-2,5-diyl, naphthalene-2,6-diyl, or 1,3-thiazole-2,4(5)-diyl;

$M^1$, $M^2$, $M^3$ and $M^4$, independently of one another, are —O—, —S—, —CO—, —CO—O—, —O—CO—, —O—CO—O—, —$CH_2$—O—, —O—$CH_2$—, —$CH_2$—$CH_2$—, —CH=CH— or —C≡C—, with the proviso that two M groups must not be bonded directly to one another;

k, l, m, n, o, p and q are 0 or 1, with the proviso that the sum of l+n+p is more than 0 and less than 4.

2. The ferroelectric liquid crystal mixture as claimed in claim 1, comprising 2 to 35 compounds from groups A to E.

3. The ferroelectric liquid crystal mixture as claimed in claim 1, comprising at least 5% by weight of the compounds from groups A to E.

4. The ferroelectric liquid crystal mixture as claimed in claim 1, comprising one or more, 4-cyano-cyclohexyls of the formula (VI):

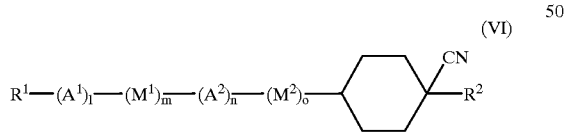

$R^1$ and $R^2$ independently of one another, are hydrogen or a a straight-chain or branched-chain alkyl group having from 2 to 16 carbon atoms (with or without an asymmetrical carbon atom), in which one or two non-adjacent —$CH_2$— groups may be replaced by —O—, —CO—, —CO—O—, —O—CO—, —CH=CH—, —C≡C— or —Si$(CH_3)_2$—; one or more hydrogen atoms of the alkyl group may be substituted by F, Cl, CN and/or $CF_3$; or $R^1$ is one of the following chiral groups:

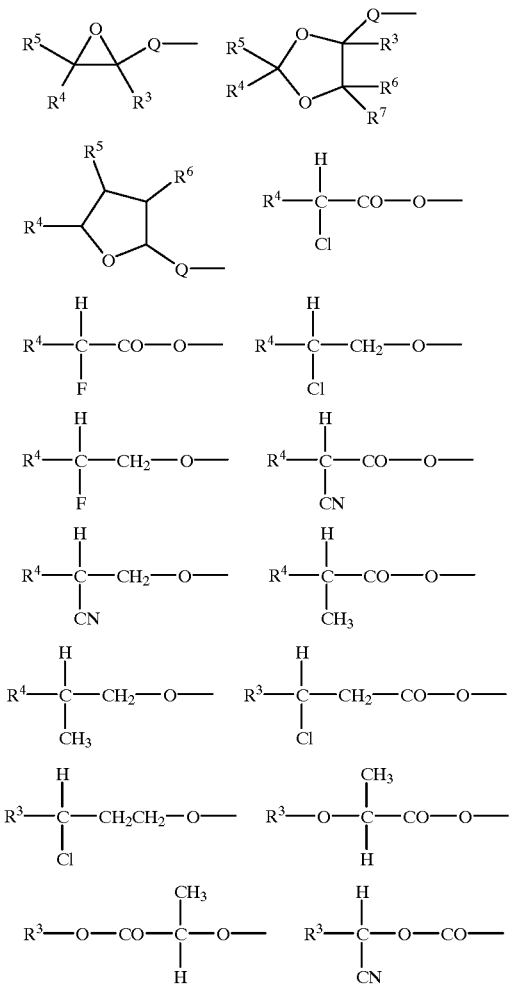

wherein $R^3$, $R^4$, $R^5$, $R^6$ and $R^7$, independently of one another, are a straight-chain or branched-chain alkyl group having from 1 to 16 carbon atoms (with or without an asymmetrical carbon atom), where one or more —$CH_2$— groups may also be substituted by —O— or —CH=CH—, with the proviso that oxygen atoms must not be bonded directly to one another; one or more hydrogen atoms of the alkyl group may be substituted by —F or —Cl; or $R^4$ and $R^5$ may also together be —$(CH_2)_4$— or —$(CH_2)_5$— if they are bonded to an oxirane, dioxolane or tetrahydrofuran system;

Q is —$CH_2$—O—, —CO—O— or a single bond;

$A^1$ and $A^2$ are identical or different and are 1,4-phenylene, in which one or more two hydrogen atoms may be substituted by F, or pyrazine-2,5-diyl, pyridazine-3,6-diyl, pyridine-2,5-diyl or pyrimidine-2,5-diyl, trans-1,4-cyclohexylene in which one or two hydrogen atoms may be substituted by CN, or 1,3,4-thiazidazole-2,5-diyl, 1,3-dioxane-2,5-diyl, naphthalene-1,6-diyl;

$M^1$ and $M^2$, independently of one another, are —CO—O—, —O—CO—, —O—CO—O—, —$CH_2$—O—, —O—$CH_2$—, —$CH_2$—$CH_2$—, —CH=CH— or —CH≡C—;

l, m, n and o are 0 or 1, with the proviso that the sum o l+n is more than 0 and less than 4.

5. The ferroelectric liquid crystal mixture as claimed in claim 1, comprising one or more phenyl pyrimidine compounds of the formula (VII),

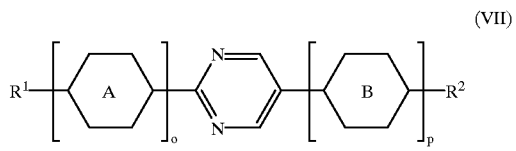

(VII)

R¹ and R² independently of one another, are
(a) a hydrogen atom,
(b) a straight-chain or branched-chain alkyl group, with or without an asymmetric carbon atom, having from 2 to 16 carbon atoms, in which one or two —CH$_2$— groups may be replaced by —O—, —S—, —CO—, —CO—O—, —O—CO—, —CH=CH—, —C≡C—, —Si(CH$_3$)$_2$—, 1,4-cyclohexylene, 1,4-phenylene, cyclopropane-1,2-diyl or —O—CO—O—, with the proviso that —O— and/or —S-atoms must not be directly bonded to one another; one or more hydrogen atoms of the alkyl group may be substituted with F, Cl, CN and/or CF$_3$; and a terminal methyl group may be substituted with a cyclopropyl group or a cyclohexyl group; or
(c) any one of the following chiral groups:

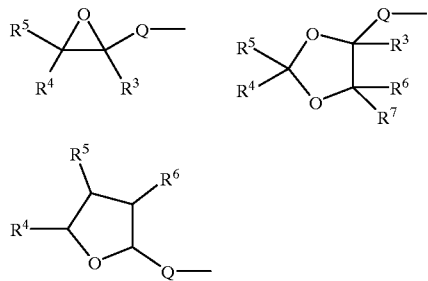

wherein R³, R⁴, R⁵, R⁶ and R⁷, independently of one another, are a straight-chain or branched-chain alkyl group having from 1 to 16 carbon atoms (with or without an asymmetrical carbon atom), where one or more —CH$_2$— groups may also be replaced by —O— or —CH=CH—, with the proviso that oxygen atoms must not be bonded directly to one another; one or more hydrogen atoms of the alkyl group may be substituted by —F or —Cl; or R⁴ and R⁵ may also together be —(CH$_2$)$_4$— or —(CH$_2$)$_5$— if they are bonded to an oxirane, dioxolane, tetrahydrofuran, system;

Q is —CH$_2$—O—, —CO—O— or a single bond;

rings A and B, independently of one another, are a phenyl group or a cyclohexyl group;

o and p are 0, 1 or 2, with the proviso that o+p≦2; if o or p are 2 the groups A or B can be different.

6. A ferroelectric liquid crystal display, comprising a ferroelectric liquid crystal mixture as claimed in claim 1.

7. A ferroelectric liquid crystal display as claimed in claim 6, which operates in the inverse mode.

8. The ferroelectric liquid crystal as claimed in claim 1, comprising compounds selected from three different groups A to E, wherein the mixture further comprises at least one compound from group A.

9. The ferroelectric liquid crystal mixture as claimed in claim 1, comprising one or more compounds from group A, one or more compounds from group B, and one or more compounds from group C to E.

10. The ferroelectric liquid crystal mixture as claimed in claim 1, comprising three or more compounds from at least groups A, B, and C.

11. The ferroelectric liquid crystal mixture as claimed in claim 1, comprising three or more compounds from at least groups A, B, and D.

12. The ferroelectric liquid crystal mixture as claimed in claim 1, comprising three or more compounds from at least groups A, B, and E.

* * * * *